US009193672B2

(12) United States Patent
Yu

(10) Patent No.: US 9,193,672 B2
(45) Date of Patent: Nov. 24, 2015

(54) HIGH PENETRATION PRODRUG COMPOSITIONS OF RETINOIDS AND RETINOID-RELATED COMPOUNDS

(76) Inventor: Chongxi Yu, Plainfield, IL (US)

( * ) Notice: Subject to any disclaimer, the term of this patent is extended or adjusted under 35 U.S.C. 154(b) by 257 days.

(21) Appl. No.: 12/503,739

(22) Filed: Jul. 15, 2009

(65) Prior Publication Data

US 2010/0010084 A1 Jan. 14, 2010

Related U.S. Application Data

(63) Continuation-in-part of application No. PCT/IB2007/050122, filed on Jan. 15, 2007.

(51) Int. Cl.
| | | |
|---|---|---|
| A61K 31/24 | (2006.01) | |
| A61K 31/20 | (2006.01) | |
| A61K 31/19 | (2006.01) | |
| A61K 31/22 | (2006.01) | |
| A61K 31/15 | (2006.01) | |
| A61K 31/13 | (2006.01) | |
| C12Q 1/02 | (2006.01) | |
| A61P 17/00 | (2006.01) | |
| A61P 27/02 | (2006.01) | |
| A61P 35/04 | (2006.01) | |
| C07C 219/10 | (2006.01) | |

(52) U.S. Cl.
CPC ........... *C07C 219/10* (2013.01); *C07C 2101/16* (2013.01)

(58) Field of Classification Search
None
See application file for complete search history.

(56) References Cited

U.S. PATENT DOCUMENTS

| | | | |
|---|---|---|---|
| 3,950,418 A | 4/1976 | Bollag et al. | |
| 4,224,244 A * | 9/1980 | Bollag et al. | 564/158 |
| 4,326,055 A | 4/1982 | Loeliger | |
| 4,588,525 A | 5/1986 | Arnold et al. | |
| 4,656,310 A | 4/1987 | Bollag et al. | |
| 4,746,509 A | 5/1988 | Haggiage et al. | |
| 4,900,478 A | 2/1990 | Gross | |
| 5,391,753 A | 2/1995 | Chandraratna | |
| 5,399,561 A | 3/1995 | Chandraratna | |
| 5,399,586 A | 3/1995 | Davies et al. | |
| 5,407,937 A | 4/1995 | Chandraratna | |
| 5,426,118 A | 6/1995 | Chandraratna et al. | |
| 5,451,605 A | 9/1995 | Chandraratna et al. | |
| 5,455,265 A | 10/1995 | Chandraratna | |
| 5,468,879 A | 11/1995 | Chandraratna | |
| 5,470,999 A | 11/1995 | Chandraratna | |
| 5,498,755 A | 3/1996 | Chandraratna et al. | |
| 5,516,904 A | 5/1996 | Chandraratna | |
| 5,534,516 A | 7/1996 | Chandraratna | |
| 5,556,996 A | 9/1996 | Beard et al. | |
| 5,559,248 A | 9/1996 | Starrett, Jr. et al. | |
| 5,599,819 A | 2/1997 | Chandraratna | |
| 5,602,135 A | 2/1997 | Chandraratna | |
| 5,616,597 A | 4/1997 | Chandraratna | |
| 5,616,712 A | 4/1997 | Teng et al. | |
| 5,618,839 A | 4/1997 | Starrett, Jr. et al. | |
| 5,648,385 A | 7/1997 | Starrett, Jr. et al. | |
| 5,648,563 A | 7/1997 | Buck et al. | |
| 5,837,728 A * | 11/1998 | Purcell | 514/529 |
| 5,972,323 A | 10/1999 | Lang et al. | |
| 6,011,049 A | 1/2000 | Whitcomb | |
| 6,437,142 B1 | 8/2002 | Hilpert et al. | |
| 6,693,135 B2 | 2/2004 | Yeager et al. | |
| 6,858,647 B2 | 2/2005 | Voegel et al. | |
| 7,052,715 B2 | 5/2006 | Fishman | |
| 7,256,210 B2 | 8/2007 | Man et al. | |
| 2004/0229920 A1 | 11/2004 | Garvey et al. | |

FOREIGN PATENT DOCUMENTS

| | | |
|---|---|---|
| CA | 2547086 A1 | 6/2005 |
| CA | 2614312 | 1/2007 |
| CA | 2348741 | 4/2010 |
| EP | 0751125 A1 | 1/1997 |
| JP | 02254425 A2 | 10/1990 |
| WO | 93/07902 | 4/1993 |
| WO | 98/01132 | 1/1998 |
| WO | 98/01138 | 1/1998 |
| WO | WO 0047589 A1 | 8/2000 |

(Continued)

OTHER PUBLICATIONS

Shaner et al. in Pesticide Biotransformation in Plants and Microorganisms (Hall, J. et al.); ACS Symposium Series, American Chemical Society: Washington, DC, 2000.*
Rautio et al in European Journal of Pharmaceutical Sciences 11 (2000) 157-163.*
Altucci et al. in Nature Reviews 6, 793-801 (2007).*
Orfanos et al. in Drugs 53(3):358-388 (1997).*
Gottardis et al. in Breast Cancer Research and Treatment 38:85-96 (1996).*
Adamson et al. in Clinical Cancer Research 7, 3034-3039 (2001).*

(Continued)

*Primary Examiner* — Dennis Heyer
(74) *Attorney, Agent, or Firm* — Perkins Coie LLP; Yingli Wang

(57) ABSTRACT

The invention provides compositions of novel high penetration compositions (HPC) or high penetration prodrugs (HPP) of retinoids and retinoid-related compounds, which are capable of crossing biological barriers with high penetration efficiency. The HPPs are capable of being converted to parent active drugs or drug metabolites after crossing the biological barrier and thus can render treatments for the conditions that the parent drugs or metabolites can. Additionally, the HPPs are capable of reaching areas that parent drugs may not be able to access or to render a sufficient concentration at the target areas and therefore render novel treatments. The HPPs can be administered to a subject through various administration routes, e.g., locally delivered to an action site of a condition with a high concentration or systematically administered to a biological subject and enter the general circulation with a faster rate.

7 Claims, 1 Drawing Sheet

(56) References Cited

FOREIGN PATENT DOCUMENTS

| WO | 03/022270 A1 | 3/2003 |
|---|---|---|
| WO | WO 2004009538 A1 | 1/2004 |
| WO | 2008/007171 A1 | 1/2008 |
| WO | 2008/010025 A1 | 1/2008 |
| WO | 2008/012602 A1 | 1/2008 |
| WO | 2008/012603 A1 | 1/2008 |
| WO | 2008/021605 A1 | 1/2008 |
| WO | 2008/017903 A1 | 2/2008 |
| WO | 2008/020270 A1 | 2/2008 |
| WO | 2008/026776 | 3/2008 |
| WO | 2008/029199 A1 | 3/2008 |
| WO | 2008/029200 A1 | 3/2008 |
| WO | 2008/044095 A1 | 4/2008 |
| WO | 2008/093173 A1 | 8/2008 |
| WO | 2008/149181 A1 | 12/2008 |

OTHER PUBLICATIONS

Laaksovirta et al. in Urology Research 27:17-22 (1999).*

Berge, S.M., et al., "Pharmaceutical Salts," J. Pharm. Sci. 66(1):1-19 (1977).

Deng, T., et al., "A New Retinoid-Like Compound that Activates Peroxisome Proliferator-Activated Receptors and Lowers Blood Glucose in Diabetic Mice," Biol. Pharm. Bull. 28(7):1192-1196 (2005).

Komori, S., et al., "On the Biological Activity of Vitamin A Derivatives (I)," Vitamin 8(3):209-213 (1955).

Korean Intellectual Property Office, International Preliminary Report on Patentability for PCT/IB2007/050122, dated Jul. 21, 2009.

Milosovich, S., et al., "Testosteronyl-4-Dimethylaminobutyrate-HCI: A Prodrug with Improved Skin Penetration Rate," J. Pharm. Sci. 82(2):227-228 (1993).

Muto, Y., et al., "Prevention of Second Primary Tumors by an Acyclic Reinoid in Patients with Hepatocellular Carcinoma," New England Journal of Medicine 340(13):1046-1047 (1999).

Sharma, P. K., et al., "Microwave Assisted Stereo Selective Synthesis of Organomercurials from All-Trans-Retinoic Acid," Main Group Metal Chemistry 28(4):207-212 (2005).

Altucci, L., et al., "RAR and RXR Modulation in Cancer and Metabolic Disease," Nat. Rev. Drug Disc. 6:793-810 (2007).

Andrews, J. M., "Determination of Minimum Inhibitory Concentrations," Journal of Antimicrobial Chemotherapy 48, suppl. S1: 5-16 (2001).

Arora, P., et al., "Design Development, Physiochemical, and In Vitro and In Vivo Evaluation of Transdermal Patches Containing Diclofenac Diethylammonium Salt," J. Pham. Sci. 91:2076-2089 (2002).

Battaglino, R., et al., "Fluoxetine Treatment Increases Trabecular Bone Formation in Mice (Fluoxetine Affects Bone Mass)," J. Cell Biochem. 100(6):1387-1394 (2007).

Choi, I., et al., "9-Cis Retinoid Acid Promotes Lymphangiogenesis and Enhances Lymphatic Vessel Regeneration: Therapeutic Implications of 9-Cis Retinoic Acid for Secondary Lymphedema," Circulation 125(7):872-882 (2012).

Dawson, M. I., et al., "The Retinoid X Receptors and Their Ligands," Biochim. Biophys. Acta 1821(1):21-56 (2012).

Drachman, D.B., et al., "Cycloxygenase 2 Inhibition Protects Motor Neurons and Prolongs Survival in a Transgenic Mouse Model of ALS," Annals of Neurology 52:771-778 (2002).

Duester, G., "Retonoic Acid Synthesis and Signaling during Early Organogenesis," Cell 134(6):921-931 (2008).

Erlanson-Albertsson, C., et al., "Enterostatin—A Peptide Regulating Fat Intake," Obes. Res. 5(4):360-372 (1997).

Georgala, S., et al., "Oral Isotretinoin in the Treatment of Recalcitrant Condylomata Acuminata of the Cervix: A Randomized Placebo Controlled Trial," Sex Transm. Infect. 80:216-218 (2000).

Ginaldi, L., et al., "Osteoporosis, Inflammation and Ageing," Immunity & Ageing 2:14 (2005).

Hovgaard, L., et al., "Drug Delivery Studies in Caco-2 Monolayers. Synthesis, Hydrolysis, and Transport of O-Cyclopropane Carboxylic Acid Ester Prodrugs of Various B-Blocking Agents," Pharm. Res. 12(3):387-392 (1995).

Hovgaard, L., et al., "Permeation Studies on O-Cyclopropanoyl Ester Prodrugs of B-Blockers in Caco-2 Cell Monolayers," Proceed. Intern: Symp. Control. Rel. Bioact. Mater. 20:238-239 (1993).

Laaksovirta, S., et al., "The Cytostatic effect of 9-Cis-Retinoic Acid, Tretinoin, and Isotretinoin on Three Different Human Bladder Cancer Cell Lines In Vitro," Urol. Res. 27:17-22 (1999).

Mao, J. T., et al., "A Pilot Study of All-trans-Retinoic Acid for the Treatment of Human Emphysema," Am. J. Respir. Crit. Care Med. 165:718-723 (2002).

Marshall, H., et al., "Retinoids and Hox Genes," FASEB J. 10:969-978 (1996).

Meng-er, H., et al., "Use of All-Trans Retinoic Acid in the Treatment of Acute Promyelocytic Leukemia," Blood 72(2):567-572 (1988).

Moore, T., et al., "The Production of Experimental Vitamin A Deficiency in Rats and Mice," Lab. Animals 5:239-250 (1971).

Nelson, A. M., et al., "Neutrophil Gelatinase-Associated Lipocalin Mediates 13-cis Retinoic Acid-Induced Apoptosis of Human Sebaceous Gland Cells," J. Clin. Invest. 118:1468-1478 (2008).

Nelson, A. M., et al., "13-cis Retinoic Acid Induces Apoptosis and Cell Cycle Arrest in Human SEB-1 Sebocytes," J. Invest. Dermatol. 126:2178-2189 (2006).

Pan, D. S., et al., "Inhibitory Effect of Progesterone on Inflammatory Factors after Experimental Traumatic Brain Injury," Biomed. Environ. Sci. 20(5):432-438 (2007).

Pendino, F., et al., "Retinoids Down-Regulate Telomerase and Telomere Length in a Pathway Distinct from leukemia Cell Differentiation," PNAS 98(12):6662-6667 (2001).

Raisz, L., "Pathogenesis of Osteoporosis: Concepts, Conflicts, and Prospects," J. Clin. Invest. 115(12):3318-3325 (2005).

Roof, R. L., et al., "Gender Differences in Acute CNS Trauma and Stroke: Neuroprotective Effects of Estrogen and Progesterone," J. Neurotrauma 17(5):367-388 (2000).

Sanz, M. A., "Treatment of Acute Promyelocytic Leukemia," Hematology 147-155 (2006).

Scott, I. L., "Keystone Symposia: Inflammation and Cancer, Breckenridge, CO, USA, Feb. 27-Mar. 3, 2005," Technical Reports 10(13)1-17.

Shalinsky, D. R., et al., "Enhanced Antitumor Efficacy of Cisplatin in Combination with ALRT1057 (9-Cis Retinoic Acid) in Human Oral Squamous Carcinoma Xenografts in Nude Mice," Clin. Cancer Res. 2:511-520 (1996).

Shimshoni, J. A., et al., "Stereoselective Formation and Metabolism of 4-Hydroxy-Retinoic Acid Enantiomers by Cytochrome P450 Enzymes," J. Biol. Chem. 287(50):42223-42232 (2012).

Sorhede, M., et al., "Enterostatin: A Gut-Brain Peptide Regulating Fat Intake in Rat," J. Physiol. 87(4):273-275 (1993).

Tozkoparan, B., et al.,"6-Benzylidenethiazolo[3,2-b]-1,24-Triazole-5(6H)-Ones Sybstituted with Ibprofen: Synthesis, Characterization and Evaluation of Anti-Inflammatory Activity," Eur. J. Med. Chem. 35(7-8):743-750 (2000).

Van Beek, M. E. A. B., et al., "Spermatogenesis in Retinol-Deficient Rats Maintained on Retinoic Acid," J. Reprod. Fert. 94:327-336 (1992).

Wright, D. W., et al., "ProTECT: A Randomized Clinical Trial of Progesterone for Acute Traumatic Brain Injury," Ann. Emerg. Med. 49(4):391-402 (2007).

Xiao, G., et al., "Improved Outcomes from the Administration of Progesterone for Patients with Acute Severe ttraumatic bbrain iinjury: A Randomized Controlled Trial," Crit. Care 12:R61 (2008).

Yang, S., et al., "Specificity of RGS10A as a Key Component in the RANKL Signaling Mechanism for Osteoclast Differentiation," J. Cell Sci. 120:3362-3371 (2007).

Zhao, Z., et al., "Effect of 9-cis-Retinoic Acid on Growth and RXR Expression in Human Breast Cancer Cells," Exp. Cell Res. 219(2):555-561 (1995).

Zhou, Q., et al., "Expression of Stimulated by Retinoic Acid Gene 8 (Stra8) in Spermatogenic Cells Induced by Retinoic Acid: An In Vivo Study in Vitamin A-Sufficient Postnatal Murine Testes," Biol. Reprod. 79:35-42 (2008).

* cited by examiner

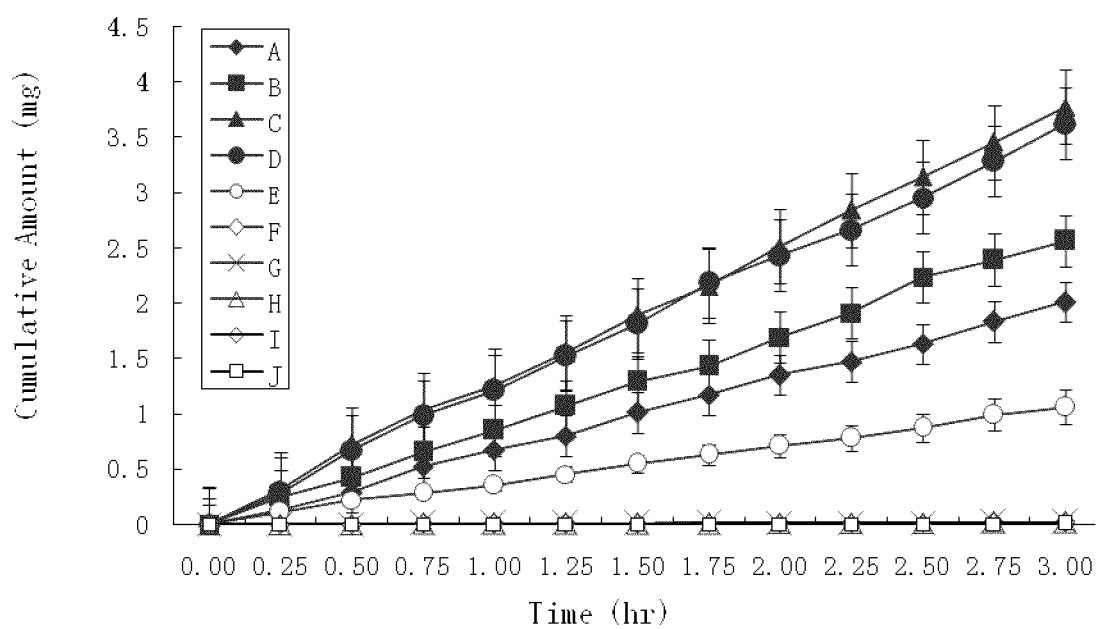

HIGH PENETRATION PRODRUG COMPOSITIONS OF RETINOIDS AND RETINOID-RELATED COMPOUNDS

CROSS-REFERENCE TO RELATED APPLICATIONS

The present application is a continuation-in-part application of International Application PCT/IB2007/050122, filed Jan. 15, 2007 and published Jul. 24, 2008 with International Publication Number WO2008/087493, which is incorporated herein by reference in its entirety.

FIELD OF THE INVENTION

This invention relates to the field of pharmaceutical compositions capable of penetrating one or more biological barriers and methods of using the pharmaceutical compositions for preventing, diagnosing and/or treating condition or disease in human and animals that are treatable by retinoid or retinoid-related compounds. The invention also relates to methods of using the pharmaceutical compositions for screening new drug candidates and methods of using the pharmaceutical compositions for diagnosing a condition in a biological subject.

BACKGROUND OF THE INVENTION

Retinoids are a class of compounds that comprise a four-isoprenoid unit in their molecular structures. Examples of retinoids include retinol (vitamin A), retinal, retiferol, tretinoin (all-trans-retinoic acid, e.g. retinoic acid, Retin-A), isotretinoin, alitretinoin (9-cis-retinoic acid), etretinate, acitretin, tazarotene, bexarotene and Adapalene.

Retinoids and retinoid-related compounds have important and diverse functions in a biological system, and have been used to treat various conditions such as acne, photoaging, psoriasis, ichthyosis, hair loss and tumor. However, time and/or dosage related adverse effects have been also reported. Examples of adverse effects of retinoids and retinoid-related compounds include painful tender swellings on the long bones, anorexia, skin lesions, hair loss, hepatosplenomegaly, papilloedema, bleeding, general malaise, pseudotomor cerebri and even death.

One alternative method of drug administration is topical delivery. Topical drug delivery has several advantages. This method avoids inactivation of a drug caused by first pass metabolism in the liver and gastrointestinal tract. It also provides local delivery of appropriate concentrations of a drug to the intended site of action without systemic exposure. Fishman (Fishman; Robert, U.S. Pat. No. 7,052,715) indicated that an additional problem associated with oral medications, is that the concentration levels which must be achieved in the bloodstream must be significant in order to effectively treat distal areas of pain, inflammation, or infection. These levels are often much higher than would be necessary if the drugs were accurately delivered to the particular site of pain or injury. For most of retinoids, topical administration cannot deliver an effective therapeutic level.

Therefore, a need exists in the art for novel compositions that are capable of being delivered efficiently and effectively to the action site of a condition (e.g., a disease) to prevent, reduce or treat conditions as well as minimize adverse side effects.

SUMMARY OF THE INVENTION

One aspect of the invention is directed to a high penetration prodrug (HPP) or high penetration composition (HPC) comprising a functional unit covalently linked to a transportational unit through a linker. The terms "HPP" and "HPC" are used alone or together herein and are interchangeable unless specifically noted.

In certain embodiments, a functional unit of a HPP or HPC comprises a moiety of an agent, wherein the efficient and effective delivery of the agent to a biological subject and/or transportation of the agent across one or more biological barriers are/is desired.

In certain embodiments, a functional unit may be hydrophilic, lipophilic, or amphiphilic (i.e., both hydrophilic and lipophilic). For example, the lipophilic nature of a function unit may be inherent or achieved by converting the hydrophilic moieties of a functional unit to lipophilic moieties. In certain embodiments, a carboxyl group, amino group, guanidine group or other hydrophilic group of a functional unit is protected with an alkyl, aryl, or heteroaryl ester or amide group to make the HPP or HPC more lipophilic.

In certain embodiments, a functional unit of a HPP or HPC comprises a moiety of a retinoid or retinoid-related compound. A retinoid-related compound is a compound comprising a retinoid structure, a retinoid metabolite, or an agent that can be metabolized into a retinoid or retinoids metabolite after a HPP or HPC penetrates one or more biological barriers. A retinoid-related compound further includes a compound that is an analog or mimic of a retinoid or a retinoid metabolite, or an agent that can be metabolized into an analogue or mimic of a retinoid or a retinoid metabolite, after a HPP or HPC penetrates one or more biological barriers. Examples of retinoids include retinol (vitamin A), retinal, retiferol, tretinoin (all-trans-retinoic acid, e.g. retinoic acid, Retin-A), isotretinoin, alitretinoin (9-cis-retinoic acid), etretinate, acitretin, tazarotene, bexarotene and Adapalene.

In certain embodiments, a transportational unit of a HPP or HPC comprises a protonatable amine group that is capable of facilitating or enhancing the transportation or crossing of the HPP or HPC through one or more biological barriers. In certain embodiments, the protonatable amine group is substantially protonated at the pH of the biological barriers through which a HPP or HPC penetrates. In certain embodiments, the amine group can be reversibly protonated or deprotonated.

In certain embodiments, a linker covalently links the functional unit to the transportational unit of a HPP and comprises a bond that is capable of being cleaved after the HPP penetrates across one or more biological barriers. The cleavable bond comprises, for example, a covalent bond, an ether, a thioether, an amide, an ester, a thioester, a carbonate, a carbamate, a phosphate or an oxime bond.

In certain embodiments, a HPP or HPC of a retinoid or retinoid-related compound comprises one or two primary, secondary or tertiary amine groups that exist in the protonated form at physiological pH. In certain embodiments, the HPP or HPC comprises one primary, secondary or tertiary amine group that exists in the protonated form at physiological pH.

Another aspect of the invention relates to a pharmaceutical composition comprising at least one HPP or HPC of a retinoid or retinoid-related compound and a pharmaceutically acceptable carrier.

Another aspect of the invention relates to a method for penetrating a biological barrier using a HPP or HPC of a retinoid or retinoid-related compound.

Another aspect of the invention relates to a method for diagnosing the onset, development, or remission of a condition in a biological subject by using a HPP or HPC of a retinoid or retinoid-related compound. In certain embodiments, the HPP (or HPC) or the functional unit thereof is detectable. In certain embodiments, the HPP or the functional unit of the HPP is inherently detectable, labeled with, or conjugated to, a detectable marker.

Another aspect of the invention relates to a method for screening functional units, linkers, or transportational units for desired characteristics.

Another aspect of the invention relates to a method for preventing, ameliorating, or treating a condition in a biological subject by administering to the subject a composition in accordance with the invention. In certain embodiments, the method relates to treating a condition in a subject treatable by retinoids or retinoid-related compounds by administering to the subject a therapeutically effective amount of a HPP of a retinoid or retinoid-related compound, or a pharmaceutical composition thereof. In certain embodiments, the conditions treatable by the method include, without limitation, Vitamin A deficiency conditions (e.g. nyctalopia, keratomalacia, keratinization, dry skin, lowered resistance to infection, decreased growth rate, slow bone development, thickening of bone, diminished production of cortical steroids, and fetal malformations), infection-related conditions (e.g. herpes simplex infections and lowered resistance to infections), skin conditions (e.g. keratinization, dry skin, skin damage through sun exposure (e.g. photoaging), hyperpigmented macules (liver spot), wrinkles, elastosis and premature aging (e.g. wrinkles), drug-induced photosensitivity, diminished production of cortical steroids, epidermal wound healing, keloids, hyperkeratotic skin disease, Darier's disease, lamellar ichthyosis, pityriasis rubra pilaris, lichen planus, refractory rosacea, keratosis palmaris et plantaris, leukoplakia, xeroderma pigmentosum, Kaposi's sarcoma, AIDS-related Kaposi's sarcoma, cutaneous T-cell lymphoma (CTCL), hyperproliferative skin diseases (e.g. psoriasis, basal cell carcinomas), disorders of keratinization and keratosis, neoplastic diseases, disorders of the sebaceous glands (e.g. acne vulgaris, recalcitrant cystic acne, acne and seborrhoic dermatitis)), eye conditions (e.g. nyctalopia, keratinization, xerophthalmia and Grover's disease), bone conditions (e.g. bone thickening and myelodysplastic syndromes), hair loss, tumor and related conditions (e.g. benign tumor, breast cancer, colon-rectum cancer, lung or other respiratory system cancers, skin cancer, basal cell carcinoma, cervical cancer, mycosis fungoides, cutaneous T-cell lymphoma (CTCL), squamous cell skin cancer, second primary tumors, head and neck carcinoma, ovarian cancer, prostate cancer, and renal cell cancer), and metabolic disorders (e.g. diabetes such as type 2 diabetes).

In certain embodiments, a pharmaceutical composition of a HPP or HPC is administrated to a biological subject via various routes including, but not limited to, oral, enteral, buccal, nasal, topical, rectal, vaginal, aerosol, transmucosal, epidermal, transdermal, dermal, ophthalmic, pulmonary, subcutaneous, and/or parenteral routes. In certain preferred embodiments, a pharmaceutical composition of a HPP or HPC is administered orally, transdermally, topically, subcutaneously and/or parenterally.

In accordance with the advantages of the invention, without intending to be limited by any particular mechanism, a therapeutically effective amount of a HPP or HPC can be administered locally to a site of condition with a less dosage at a higher concentration. The advantages of the invention also include, for example, avoidance of systematic administration, reduction of adverse effects (e.g., pain of injection, gastrointestinal/renal effects, and other side effect), and possible novel treatments due to high local concentration of a HPP, HPC or active agent. The advantages further include, for example, systematic administration of a HPP or HPC to a biological subject to achieve faster and more efficient bioavailability, penetration of biological barriers (e.g., the blood brain barrier) which have been difficult to cross, and new indications as a result of passing through biological barriers.

BRIEF DESCRIPTION OF THE FIGURES

FIG. 1: Cumulative amounts of 9-cis-retinoic acid 1-piperidineethyl ester.HBr (5% solution, A), N,N-diethylaminoethyl 13-cis-retinoate.HBr (5% solution, B), N,N-diethylaminoethyl all-trans-retinoate.HBr (5% solution, C), retinyl N,N-dimethyl-2-aminoacetate.HCl (5% solution, D), N,N-diethylaminoethyl 4-[1-(5,6,7,8-tetrahydro-3,5,5,8,8-pentamethyl-2-naphthalenyl)ethenyl]benzoate.HCl (5% solution, E),9-cis-retinoic acid (5% suspension, F), 13-cis-retinoic acid (5% suspension, G), all-trans-retinoic acid (5% suspension, H), vitamin A (5% suspension, I), and bexaroten (5% suspension, J), crossing isolated human skin tissue in Franz cells (n=5). In each case, the vehicle was a pH 7.4 phosphate buffer (0.2 M).

DETAILED DESCRIPTION OF THE INVENTION

I. Structures of High Penetration Prodrug (HPP) or High Penetration Composition (HPC)

One aspect of the invention is directed to a high penetration prodrug (HPP) or a high penetration composition (HPC). The term "high penetration prodrug" or "HPP" or "high penetration composition" or "HPC" as used herein refers to a composition comprising a functional unit covalently linked to a transportational unit through a linker.

A functional unit of a HPP or HPC which comprises a moiety of a parent drug has the properties of: 1) the delivery of the parent drug or the HPP/HPC into a biological subject and/or the transportation of the parent drug across a biological barrier are/is desired, 2) the HPP/HPC is capable of penetrating or crossing a biological barrier, and 3) the HPP/HPC is capable of being cleaved so as to turn the moiety of a parent drug into the parent drug or a metabolite of the parent drug.

In certain embodiments, a functional unit may be hydrophilic, lipophilic, or amphiphilic (hydrophilic and lipophilic). The lipophilic moiety of the functional unit may be inherent or achieved by converting one or more hydrophilic moieties of the functional unit to lipophilic moieties. For example, a lipophilic moiety of a functional unit is produced by converting one or more hydrophilic groups of the functional unit to lipophilic groups via organic synthesis. Examples of hydrophilic groups include, without limitation, carboxylic, hydroxyl, thiol, amine, phosphate/phosphonate, guanidine and carbonyl groups. Lipophilic moieties produced via the modification of these hydrophilic groups include, without limitation, ethers, thioethers, esters, thioesters, carbonates, carbamates, amides, phosphates and oximes. In certain embodiments, a functional unit is lipophilicized by acetylation. In certain embodiments, a functional unit is lipophilicized by esterification.

In certain embodiments, a parent drug of a HPP or HPC is selected from the group consisting of a retinoid and retinoid-related compound. The moiety of a retinoid or retinoid-related compound can be further converted to a lipophilic moiety as described supra.

Retinoids are well known in the art and are used in connection with various conditions. As used herein, a retinoid refers to a compound that comprises a four-isoprenoid unit. Examples of retinoids include retinol (vitamin A), retinal, retiferol, tretinoin (all-trans-retinoic acid, e.g. retinoic acid, Retin-A), isotretinoin, alitretinoin (9-cis-retinoic acid), etretinate, acitretin, tazarotene, bexarotene and Adapalene. Moreover, examples of retinoids include, but are not limited to chemicals comprising a structure selected from the group consisting of Structure R1, Structure R2, Structure R3, Structure R4, Structure R5, Structure R6, Structure R7, Structure R8, Structure R9, Structure R10, Structure R11, Structure R12, Structure R13, Structure R14, Structure R15, Structure R16, Structure R17, Structure R18, Structure R19, Structure R20, Structure R21, Structure R22, Structure R23, Structure R24, Structure R25, Structure R26, Structure R27, Structure R28, Structure R29, Structure R30, Structure R31, Structure R32, Structure R33, Structure R34, Structure R35, Structure R36, Structure R37, Structure R38, and Structure R39:

Structure R1
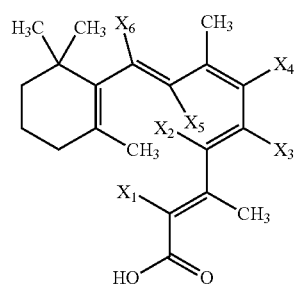

Structure R2
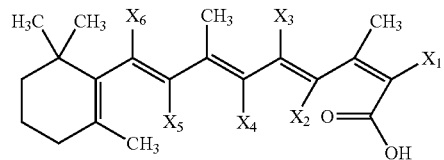

Structure R3
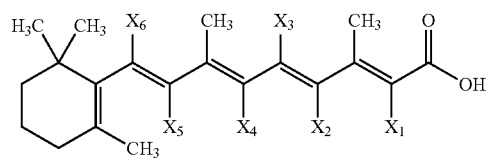

Structure R4
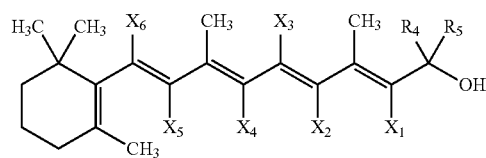

Structure R5
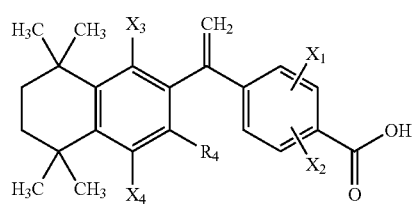

Structure R6
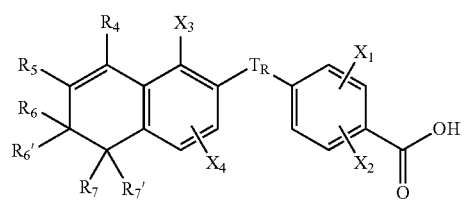

-continued

Structure R7
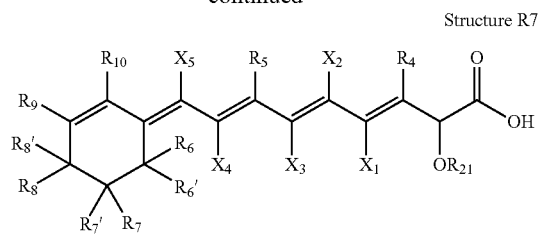

Structure R8
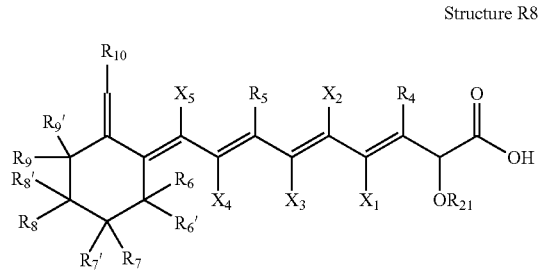

Structure R9
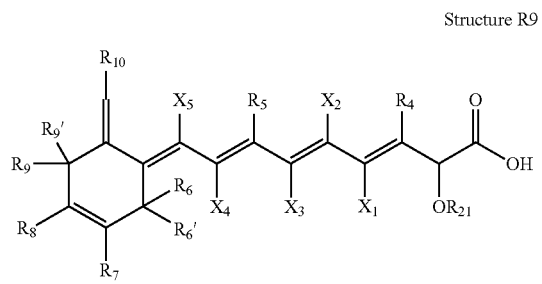

Structure R10
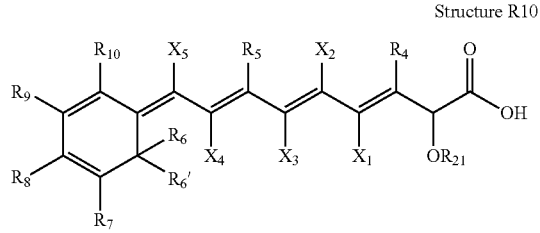

Structure R11
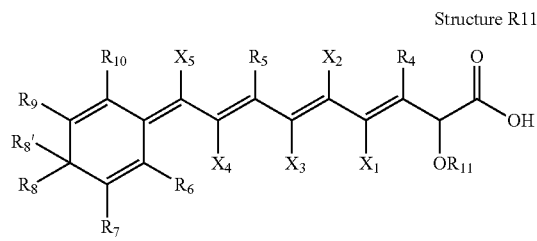

Structure R12
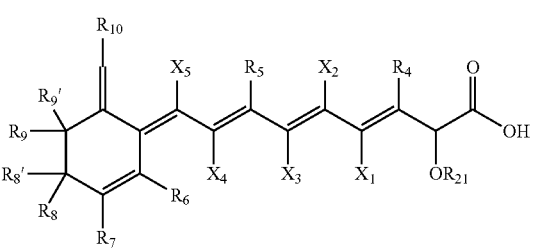

Structure R13
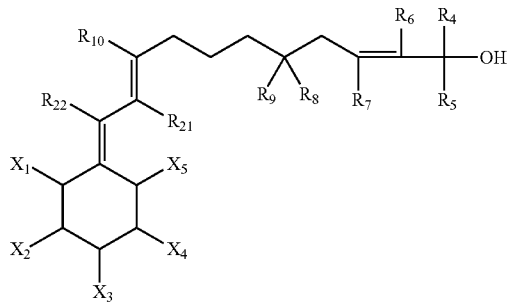
Structure R14
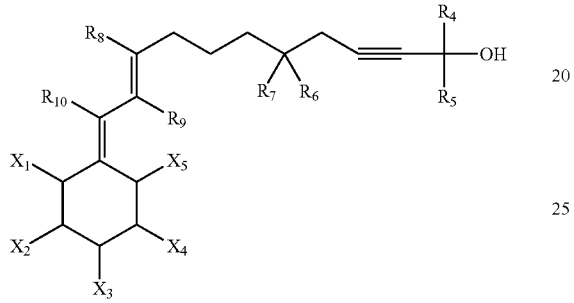
Structure R15
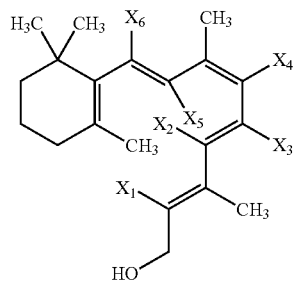
Structure R16
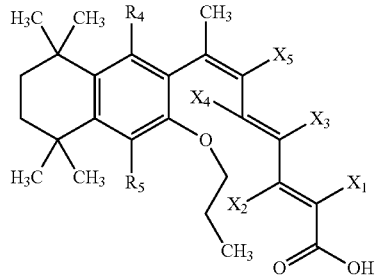
Structure R17
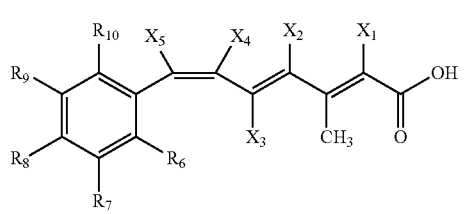
Structure R18
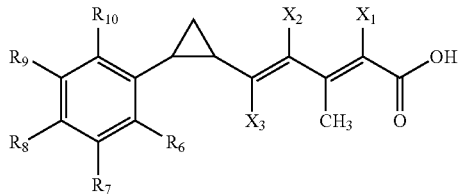
Structure R19
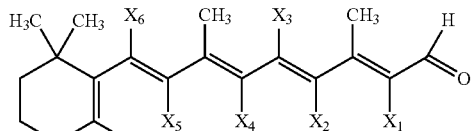
Structure R20
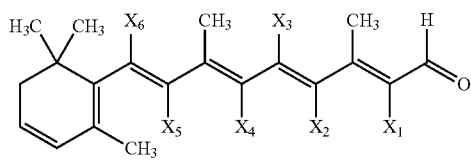
Structure R21
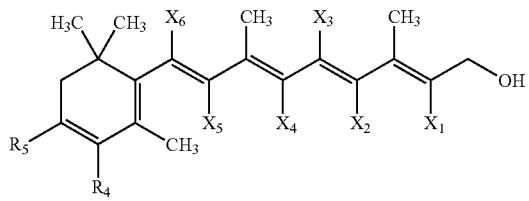
Structure R22
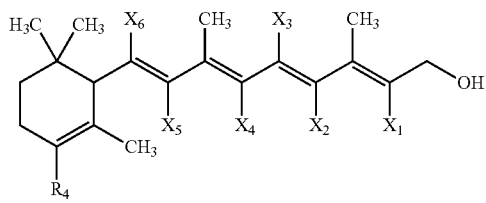
Structure R23
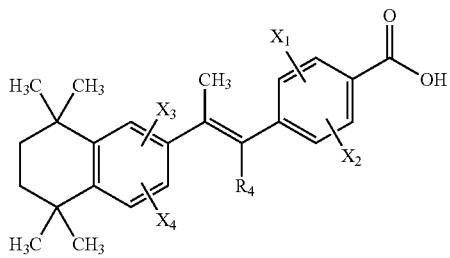

Structure R24
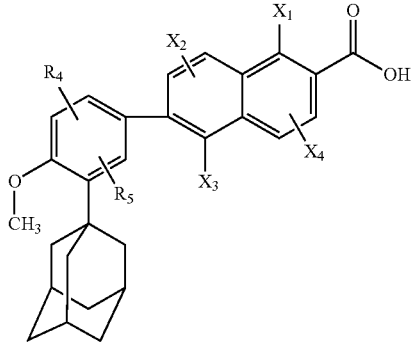
Structure R25
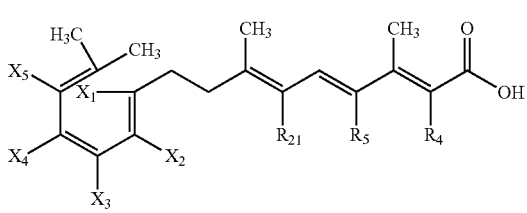
Structure R26
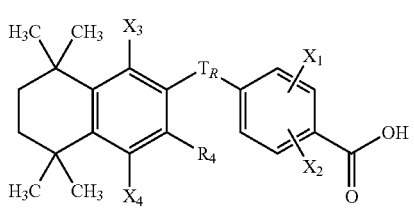
Structure R27
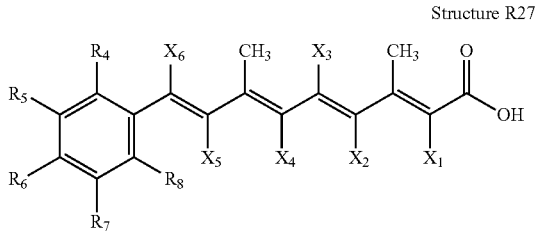
Structure R28
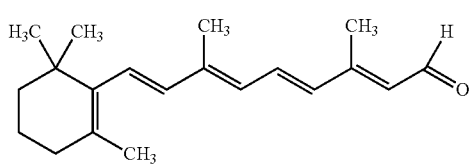
Structure R29
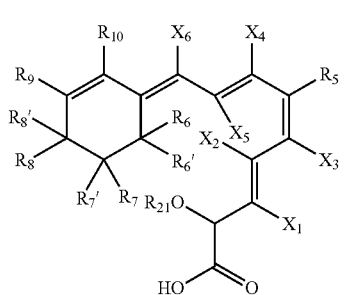
Structure R30
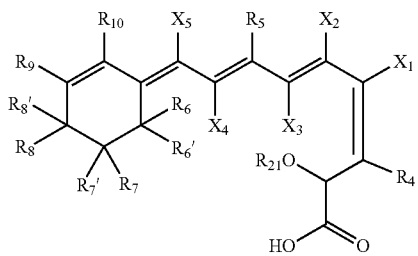
Structure R31
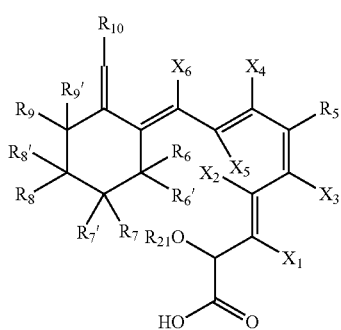
Structure R32
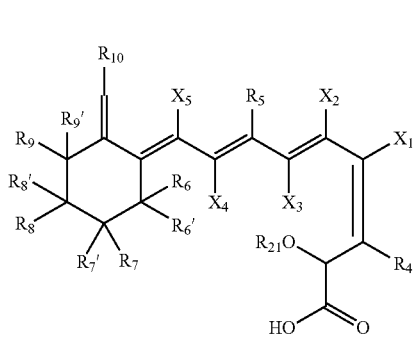
Structure R33
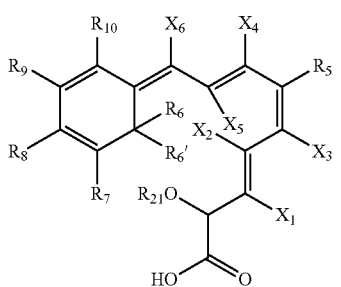
Structure R34
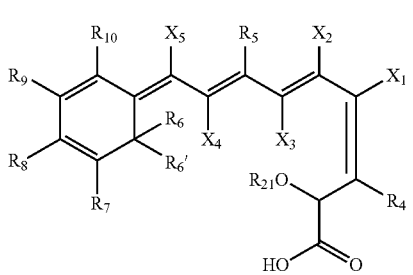

-continued

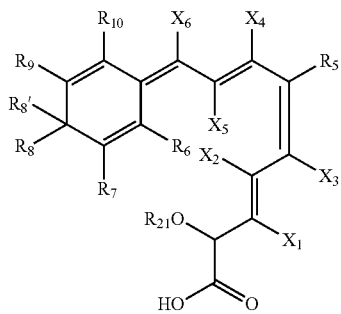

Structure R35

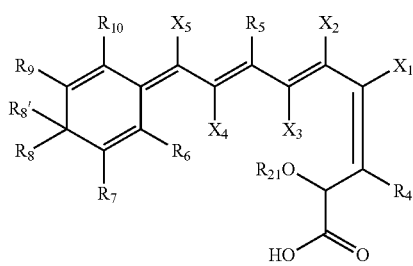

Structure R36

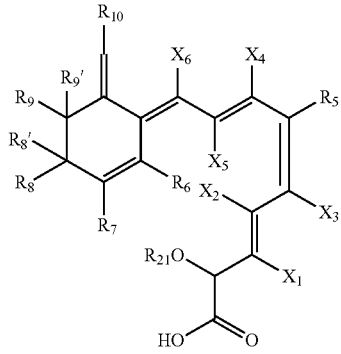

Structure R37

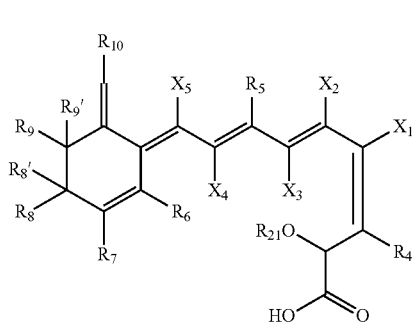

Structure R38

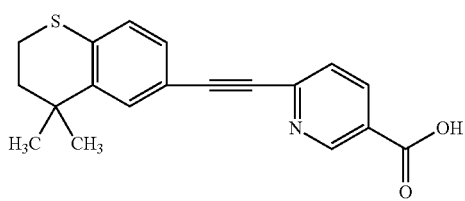

Structure R39 including stereoisomers and pharmaceutically acceptable salts thereof, wherein:

$X_1$-$X_6$ are independently selected from the group consisting of H, OH, Cl, Br, F, I, substituted and unsubstituted alkyl, substituted and unsubstituted perfluoroalkyl, and substituted and unsubstituted alkyloxy wherein in certain embodiments, the alkyl, perfluoroalkyl or alkyloxy group comprises 1-6 carbon atoms;

$R_4$ is selected from the group consisting of H, OH, Cl, Br, F, I, substituted and unsubstituted alkyl, substituted and unsubstituted alkyloxy, substituted and unsubstituted perfluoroalkyl, and substituted and unsubstituted alkyl halide, wherein in certain embodiments, the alkyl, alkyloxy, perfluoroalkyl or alkyl halide group comprises 1-6 carbon atoms;

$R_5$ is selected from the group consisting of H, OH, Cl, Br, F, I, substituted and unsubstituted alkyl, substituted and unsubstituted alkyloxy, substituted and unsubstituted perfluoroalkyl, and substituted and unsubstituted alkyl halide, wherein in certain embodiments, the alkyl, alkyloxy, perfluoroalkyl or alkyl halide group comprises 1-6 carbon atoms;

$R_{21}$ and $R_{22}$ are independently selected from the group consisting of H, OH, Cl, Br, F, I, substituted and unsubstituted alkyl, substituted and unsubstituted alkyloxy, substituted and unsubstituted perfluoroalkyl, and substituted and unsubstituted alkyl halide, wherein in certain embodiments, the alkyl, alkyloxy, perfluoroalkyl or alkyl halide group comprises 1-6 carbon atoms;

$R_6$ and $R_6'$ taken together is oxygen (=O) or taken alone are the same or different and independently selected from the group consisting of H, Cl, Br, F, I, OH, substituted and unsubstituted alkyl, substituted and unsubstituted alkyloxy, and substituted and unsubstituted alkyl halide, wherein in certain embodiments, the alkyl, alkyloxy, or alkyl halide group comprises 1-6 carbon atoms;

$R_7$ and $R_7'$ taken together is oxygen (=O) or taken alone are the same or different and independently selected from the group consisting of H, Cl, Br, F, I, OH, substituted and unsubstituted alkyl, substituted and unsubstituted alkyloxy, and substituted and unsubstituted alkyl halide, wherein in certain embodiments, the alkyl, alkyloxy, or alkyl halide group comprises 1-6 carbon atoms;

$R_8$ and $R_8'$ taken together is oxygen (=O) or taken alone are the same or different and independently selected from the group consisting of H, Cl, Br, F, I, OH, substituted and unsubstituted alkyl, substituted and unsubstituted alkyloxy, and substituted and unsubstituted alkyl halide, wherein in certain embodiments, the alkyl, alkyloxy, or alkyl halide group comprises 1-6 carbon atoms;

$R_9$ and $R_9'$ taken together is oxygen (=O) or taken alone are the same or different and independently selected from the group consisting of H, Cl, Br, F, I, OH, substituted and unsubstituted alkyl, substituted and unsubstituted alkyloxy, and substituted and unsubstituted alkyl halide, wherein in certain embodiments, the alkyl, alkyloxy, or alkyl halide group comprises 1-6 carbon atoms;

$R_{10}$ is selected from the group consisting of H, Cl, Br, F, I, OH, substituted and unsubstituted alkyl, substituted and unsubstituted alkyloxy, and substituted and unsubstituted alkyl halide, wherein in certain embodiments, the alkyl, alkyloxy, or alkyl halide group comprises 1-6 carbon atoms; and $T_R$ is selected from the group consisting of —$CH_2$=C—, —CH=CH—, —C≡C—, —C(=O)NH—, —C(=S)NH—, —C(=O)O—, —OC(=O)—, —C(=O)S—, —C(=O)$CH_2$, and —$CH_2$C(=O)—.

A retinoid-related compound is a compound comprising a retinoid structure, a retinoid metabolite, or an agent that can be metabolized into a retinoid or retinoids metabolite after a HPP or HPC penetrates one or more biological barriers. A retinoid-related compound further includes a compound that is an analog or mimic of a retinoid or a retinoid metabolite, or an agent that can be metabolized into an analog or mimic of a retinoid or a retinoid metabolite, after a HPP or HPC penetrates one or more biological barriers.

In certain embodiments, a functional unit of a HPP of a retinoid or retinoid-related compound comprises a moiety having a structure selected from the group consisting of Structure F1, Structure F2, Structure F3, Structure F4, Structure F5, Structure F6, Structure F7, Structure F8, Structure F9, Structure F10, Structure F11, Structure F12, Structure F13, Structure F14, Structure F15, Structure F16, Structure F17, Structure F18, Structure F19, Structure F20, Structure F21, Structure F22, Structure F23, Structure F24, Structure F25, Structure F26, Structure F27, Structure F28, Structure F29, Structure F30, Structure F31, Structure F32, Structure F33, Structure F34, Structure F35, Structure F36, Structure F37, Structure F38, Structure F39, Structure F40 and Structure F41:

Structure F1
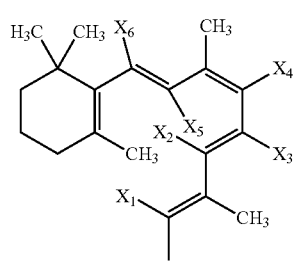

Structure F2
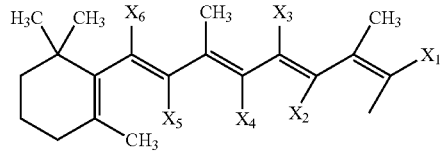

Structure F3
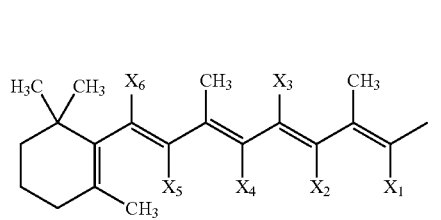

Structure F4
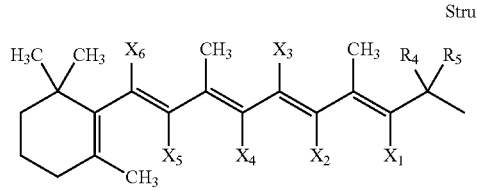

Structure F5
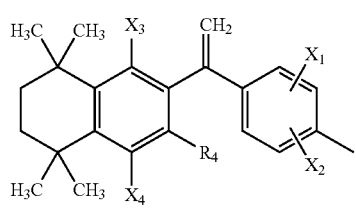

Structure F6
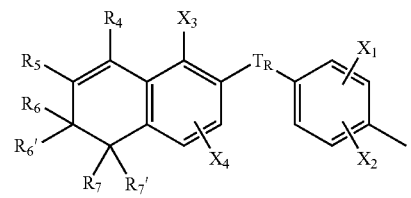

Structure F7
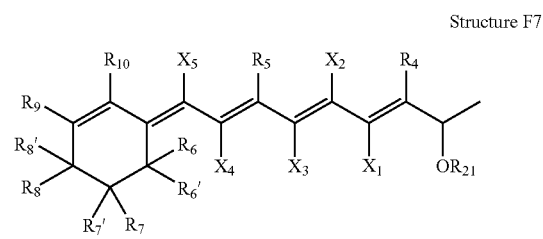

Structure F8
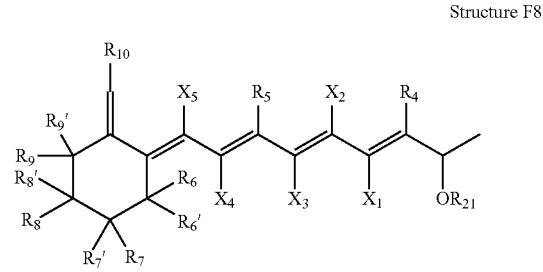

Structure F9
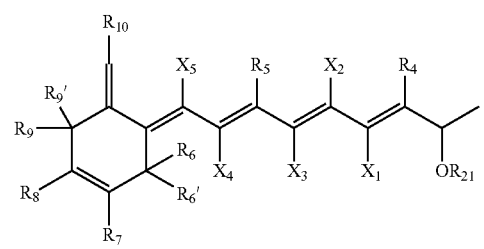

Structure F10
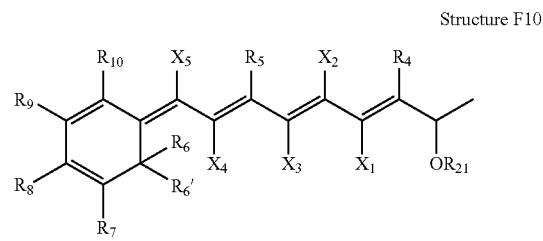

Structure F11
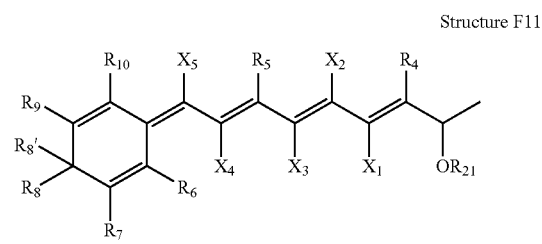

Structure F12
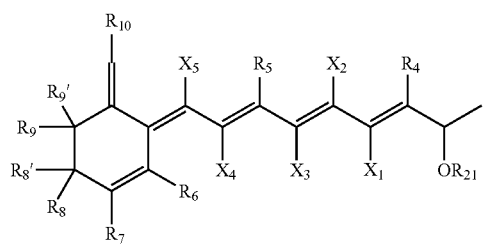
Structure F13
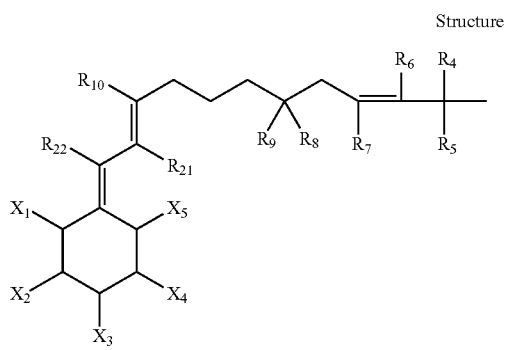
Structure F14
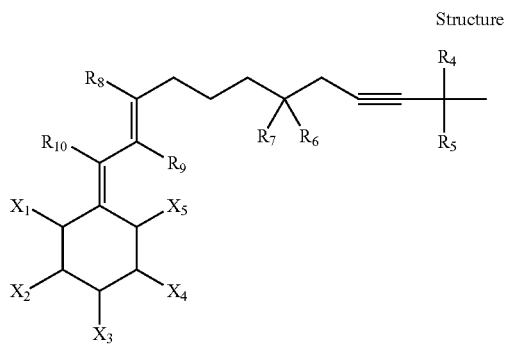
Structure F15
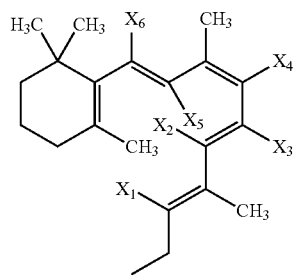
Structure F16
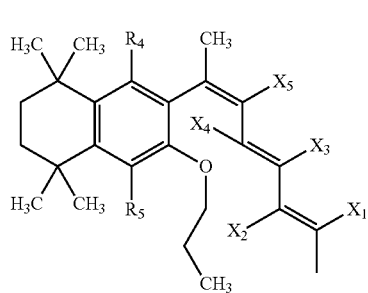
Structure F17
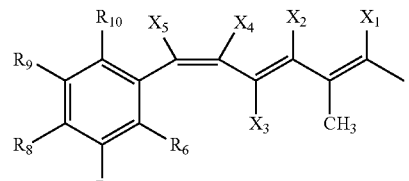
Structure F18
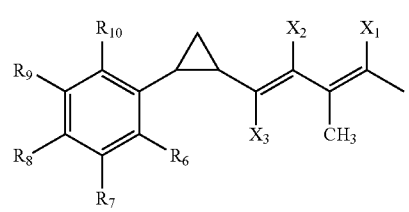
Structure F19
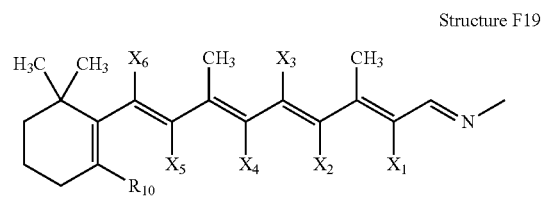
Structure F20
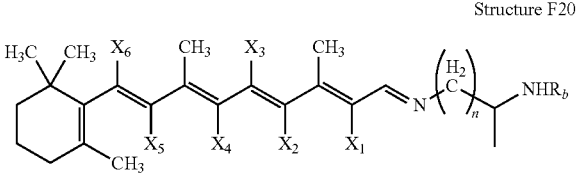
Structure F21
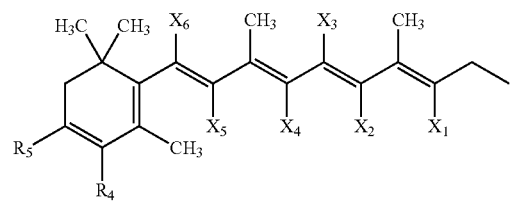
Structure F22
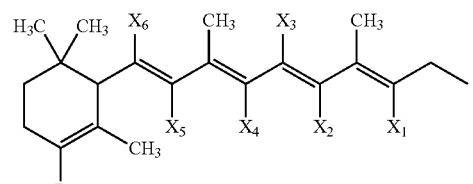
Structure F23
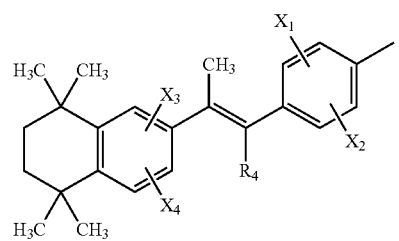

-continued
Structure F24
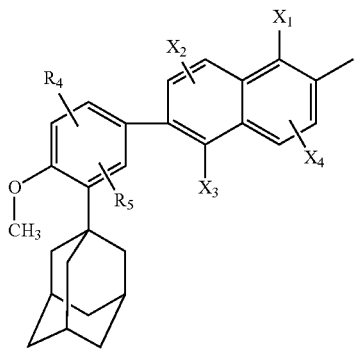
Structure F25
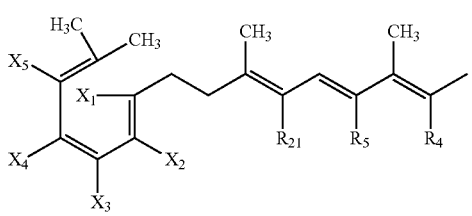
Structure F26
Structure F27
Structure F28
Structure F29
-continued
Structure F30
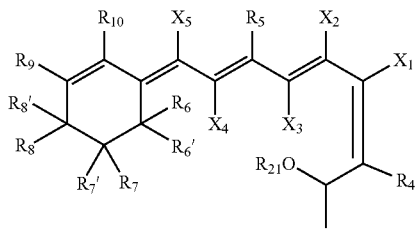
Structure F31
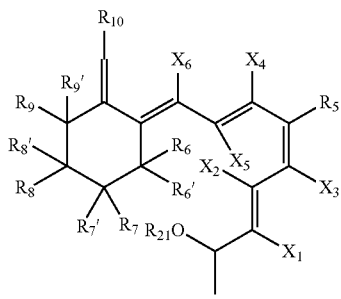
Structure F32
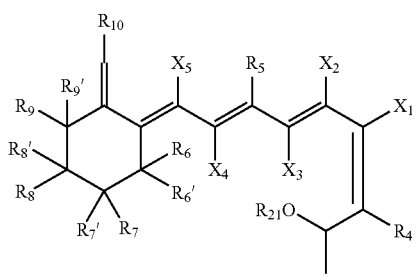
Structure F33
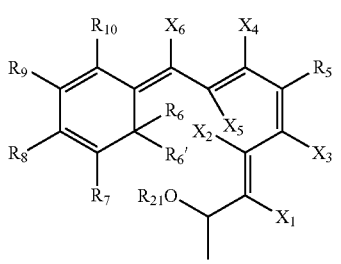
Structure F34
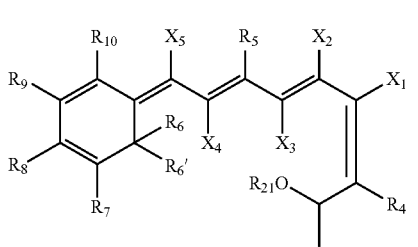
Structure F35
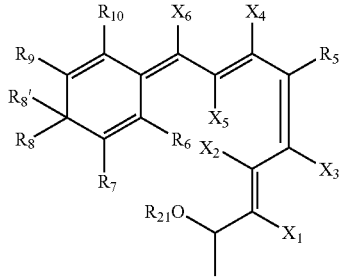

-continued

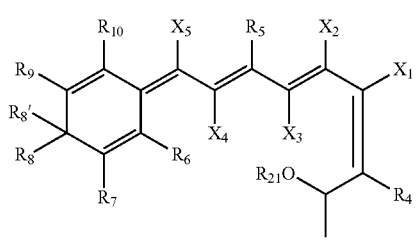

Structure F36

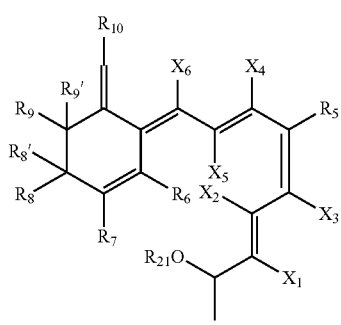

Structure F37

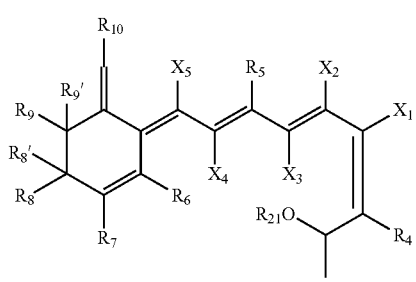

Structure F38

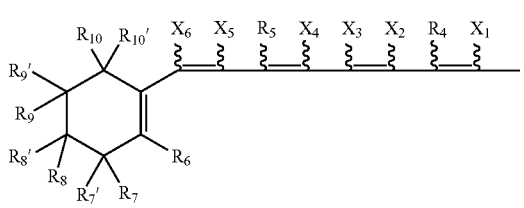

Structure F39

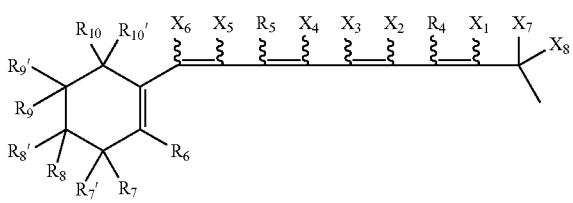

Structure F40

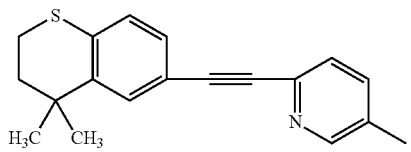

Structure F41 including stereoisomers and pharmaceutically acceptable salts thereof, wherein:

$R_1$ is selected from the group consisting of H, substituted and unsubstituted alkyl, substituted and unsubstituted alkyloxyl, substituted and unsubstituted alkenyl, substituted and unsubstituted alkynyl, substituted and unsubstituted aryl and substituted and unsubstituted heteroaryl residues;

$R_2$ is selected from the group consisting of H, substituted and unsubstituted alkyl, substituted and unsubstituted alkyloxyl, substituted and unsubstituted alkenyl, substituted and unsubstituted alkynyl, substituted and unsubstituted aryl and substituted and unsubstituted heteroaryl residues;

X is selected from the group consisting of O, S, and NH;

$X_1$-$X_8$ are independently selected from the group consisting of H, OH, Cl, Br, F, I, substituted and unsubstituted alkyl, substituted and unsubstituted perfluoroalkyl, and substituted and unsubstituted alkyloxy wherein in certain embodiments, the alkyl, perfluoroalkyl or alkyloxy group comprises 1-6 carbon atoms;

$R_4$ is selected from the group consisting of H, OH, Cl, Br, F, I, substituted and unsubstituted alkyl, substituted and unsubstituted alkyloxy, substituted and unsubstituted perfluoroalkyl, and substituted and unsubstituted alkyl halide, wherein in certain embodiments, the alkyl, alkyloxy, perfluoroalkyl or alkyl halide group comprises 1-6 carbon atoms;

$R_5$ is selected from the group consisting of H, OH, Cl, Br, F, I, substituted and unsubstituted alkyl, substituted and unsubstituted alkyloxy, substituted and unsubstituted perfluoroalkyl, and substituted and unsubstituted alkyl halide, wherein in certain embodiments, the alkyl, alkyloxy, perfluoroalkyl or alkyl halide group comprises 1-6 carbon atoms;

$R_{21}$ and $R_{22}$ are independently selected from the group consisting of H, OH, Cl, Br, F, I, substituted and unsubstituted alkyl, substituted and unsubstituted alkyloxy, substituted and unsubstituted perfluoroalkyl, and substituted and unsubstituted alkyl halide, wherein in certain embodiments, the alkyl, alkyloxy, perfluoroalkyl or alkyl halide group comprises 1-6 carbon atoms;

$R_6$ and $R_6'$ taken together is oxygen (=O) or taken alone are the same or different and independently selected from the group consisting of H, Cl, Br, F, I, OH, substituted and unsubstituted alkyl, substituted and unsubstituted alkyloxy, and substituted and unsubstituted alkyl halide, wherein in certain embodiments, the alkyl, alkyloxy, or alkyl halide group comprises 1-6 carbon atoms;

$R_7$ and $R_7'$ taken together is oxygen (=O) or taken alone are the same or different and independently selected from the group consisting of H, Cl, Br, F, I, OH, substituted and unsubstituted alkyl, substituted and unsubstituted alkyloxy, and substituted and unsubstituted alkyl halide, wherein in certain embodiments, the alkyl, alkyloxy, or alkyl halide group comprises 1-6 carbon atoms;

$R_8$ and $R_8'$ taken together is oxygen (=O) or taken alone are the same or different and independently selected from the group consisting of H, Cl, Br, F, I, OH, substituted and unsubstituted alkyl, substituted and unsubstituted alkyloxy, and substituted and unsubstituted alkyl halide, wherein in certain embodiments, the alkyl, alkyloxy, or alkyl halide group comprises 1-6 carbon atoms;

$R_9$ and $R_9'$ taken together is oxygen (=O) or taken alone are the same or different and independently selected from the group consisting of H, Cl, Br, F, I, OH, substituted and unsubstituted alkyl, substituted and unsubstituted alkyloxy, and substituted and unsubstituted alkyl halide, wherein in certain embodiments, the alkyl, alkyloxy, or alkyl halide group comprises 1-6 carbon atoms;

$R_{10}$ and $R_{10}'$ taken together is oxygen (=O) or taken alone are the same or different and independently selected from the group consisting of H, Cl, Br, F, I, OH, substituted and unsubstituted alkyl, substituted and unsubstituted alkyloxy, and substituted and unsubstituted alkyl halide, wherein in certain embodiments, the alkyl, alkyloxy, or alkyl halide group comprises 1-6 carbon atoms;

$T_R$ is selected from the group consisting of —CH$_2$=C—, —CH=CH—, —C≡C—, —C(=O)NH—, —C(=S)NH—, —C(=O)O—, —OC(=O)—, —C(=O)S—, —C(=O)CH$_2$, and —CH$_2$C(=O)—;

as used herein, unless specified otherwise, the term "HA" is nothing or a pharmaceutically acceptable acid, e.g. hydrochloride, hydrobromide, hydroiodide, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid or pamoic acid; and any CH$_2$ groups may be replaced with O, S, or NH.

As used herein, the term "pharmaceutically acceptable salt" means those salts of compounds of the invention that are safe for application in a subject. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,11-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 J. PHARM. SCI. 1-19 (1977), incorporated herein by reference.

As used herein, the term "pharmaceutically acceptable acid" means acids that can form salts with compounds of the invention that are safe for application in a subject. Examples of pharmaceutically acceptable acid include, but are not limited to, e.g. hydrochloride, hydrobromide, hydroiodide, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid and pamoic acid.

As used herein, unless specified otherwise, the term "alkyl" means a branched or unbranched, saturated or unsaturated, monovalent or multivalent hydrocarbon group, including saturated alkyl groups, alkenyl groups and alkynyl groups. Examples of alkyl include, but are not limited to, methyl, ethyl, propyl, isopropyl, butyl, isobutyl, t-butyl, pentyl, hexyl, heptyl, octyl, nonyl, decyl, undecyl, dodecyl, ethenyl, propenyl, butenyl, isobutenyl, pentenyl, hexenyl, heptenyl, octenyl, nonenyl, decenyl, undecenyl, dodecenyl, ethynyl, propynyl, butynyl, isobutynyl, pentynyl, hexynyl, heptynyl, octynyl, nonynyl, decynyl, undecynyl, dodecynyl, methylene, ethylene, propylene, isopropylene, butylene, isobutylene, t-butylene, pentylene, hexylene, heptylene, octylene, nonylene, decylene, undecylene and dodecylene. In certain embodiments, the hydrocarbon group contains 1 to 30 carbons. In certain embodiments, the hydrocarbon group contains 1 to 20 carbons. In certain embodiments, the hydrocarbon group contains 1 to 12 carbons. In certain embodiments, the hydrocarbon group contains 1 to 6 carbons.

As used herein, unless specified otherwise, the term "cycloalkyl" means an alkyl which contains at least one ring and no aromatic rings. Examples of cycloalkyl include, but are not limited to, cyclopropyl, cyclobutyl, cyclopentyl, cyclohexyl, cycloheptyl, cyclooctyl, cyclononyl, cyclodecyl, cycloundecyl and cyclododecyl. In certain embodiments, the hydrocarbon chain contains 1 to 30 carbons. In certain embodiments, the hydrocarbon group contains 1 to 20 carbons. In certain embodiments, the hydrocarbon group contains 1 to 12 carbons. In certain embodiments, the hydrocarbon group contains 1 to 6 carbons.

As used herein, unless specified otherwise, the term "heterocycloalkyl" means a cycloalkyl wherein at least one ring atom is a non-carbon atom. Examples of the non-carbon ring atom include, but are not limited to, S, O and N.

As used herein, unless specified otherwise, the term "alkoxyl" means an alkyl, cycloalkyl or heterocycloalkyl, which contains one or more oxygen atoms. Examples of alkoxyl include, but are not limited to, —CH$_2$—OH, —OCH$_3$, —O-alkyl, -alkyl-OH, -alkyl-O-alkyl-, wherein the two alkyls can be the same or different.

As used herein, unless specified otherwise, the term "alkyl halide" means an alkyl, cycloalkyl or heterocycloalkyl, which contains one or more halogen atoms, wherein the halogen atoms can be the same or different. The term "halogen" means fluorine, chlorine, bromine or iodine. Examples of alkyl halide include, but are not limited to, -alkyl-F, -alkyl-Cl, -alkyl-Br, -alkyl-I, -alkyl(F)—, -alkyl(Cl)—, -alkyl(Br)— and -alkyl(I)—.

As used herein, unless specified otherwise, the term "alkylthio" means an alkyl, cycloalkyl or heterocycloalkyl, which contains one or more sulfur atoms. Examples of alkylthio include, but are not limited to, —CH$_2$—SH, —SCH$_3$, —S-alkyl, -alkyl-SH, -alkyl-5-alkyl-, wherein the two alkyls can be the same or different.

As used herein, unless specified otherwise, the term "alkylamino" means an alkyl, cycloalkyl or heterocycloalkyl, which contains one or more nitrogen atoms. Examples of alkylamino include, but are not limited to, —CH$_2$—NH, —NCH$_3$, —N(alkyl)-alkyl, —N-alkyl, -alkyl-NH$_2$, -alkyl-N-alkyl and -alkyl-N(alkyl)-alkyl wherein the alkyls can be the same or different.

As used herein, unless specified otherwise, the term "alkylcarbonyl" means an alkyl, cycloalkyl or heterocycloalkyl, which contains one or more carbonyl groups. Examples of alkylcarbonyl group include, but are not limited to, aldehyde group (—R—C(O)—H), ketone group (—R—C(O)—R'), carboxylic acid group (R—COOH), ester group (—R—COO—R'), carboxamide, (—R—COO—N(R')R''), enone group (—R—C(O)—C(R')=C(R'')R'''), acyl halide group (—R—C(O)—X) and acid anhydride group (—R—C(O)—O—C(O)—R'), wherein R', R', R'' and R''' are the same or different alkyl, cycloalkyl, or heterocycloalkyl.

As used herein, unless specified otherwise, the term "perfluoroalkyl" means an alkyl, cycloalkyl or heterocycloalkyl, which contains one or more fluoro group, including, without limitation, perfluoromethyl, perfluoroethyl, perfluoropropyl.

As used herein, unless specified otherwise, the term "aryl" means a chemical structure comprising one or more aromatic rings. In certain embodiments, the ring atoms are all carbon. In certain embodiments, one or more ring atoms are non-carbon, e.g. oxygen, nitrogen, or sulfur ("heteroaryl"). Examples of aryl include, without limitation, phenyl, benzyl, naphthalenyl, anthracenyl, pyridyl, quinoyl, isoquinoyl, pyrazinyl, quinoxalinyl, acridinyl, pyrimidinyl, quinazolinyl, pyridazinyl, cinnolinyl, imidazolyl, benzimidazolyl, purinyl, indolyl, furanyl, benzofuranyl, isobenzofuranyl, pyrrolyl, indolyl, isoindolyl, thiophenyl, benzothiophenyl, pyrazolyl, indazolyl, oxazolyl, benzoxazolyl, isoxazolyl, benzisoxazolyl, thiaxolyl, quanidino and benzothiazolyl.

In certain embodiments, a transportational unit of a HPP comprises a protonatable amine group that is capable of facilitating the transportation or crossing of the HPP through one or more biological barriers (e.g., >about 20 times, >about 50 times, >about 100 times, >about 300 times, >about 500 times faster than the parent drug). In certain embodiments, the protonatable amine group is substantially protonated at a physiological pH. In certain embodiments, the amine group can be reversibly protonated. In certain embodiments, the transportational unit may or may not be cleaved from the functional unit after the penetration of HPP through one or more biological barriers. In certain embodiments, the transportational unit may be from the functional unit, especially for retinoids that have at least a free amino group.

In certain embodiments, the protonatable amine group is selected from the group consisting of pharmaceutically acceptable substituted and unsubstituted primary amine groups, pharmaceutically acceptable substituted and unsubstituted secondary amine groups, and pharmaceutically acceptable substituted and unsubstituted tertiary amine groups.

In certain embodiments, the protonatable amine group is selected from the group consisting of Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr:

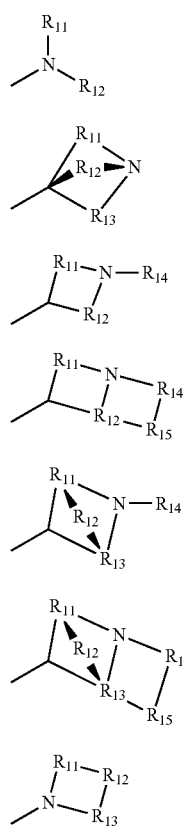

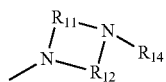
Structure Nh

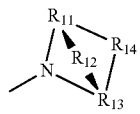
Structure Ni

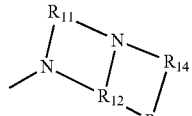
Structure Nj

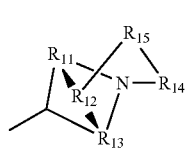
Structure Nk

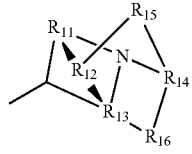
Structure Nl

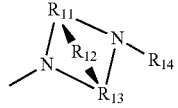
Structure Nm

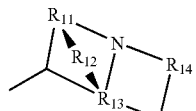
Structure Nn

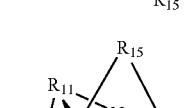
Structure No

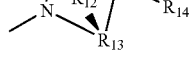
Structure Np

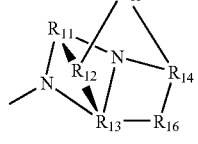
Structure Nq

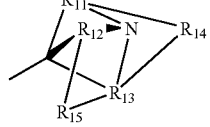
Structure Nr including stereoisomers and pharmaceutically acceptable salts thereof.

As used herein, unless specified otherwise, each $R_{11}$-$R_{16}$ is independently selected from the group consisting of nothing, H, $CH_2COOR_{11}$, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, $NR_{11}$, or any other pharmaceutically acceptable groups.

In certain embodiments, a linker covalently linking a functional unit and a transportational unit of a HPP comprises a bond that is capable of being cleaved after the HPP penetrates across one or more BBs. The cleavable bond comprises, for example, a covalent bond, an ether, thioether, amide, ester, thioester, carbonate, carbamate, phosphate or oxime bond.

In certain embodiments, a HPP of a retinoid and retinoid-related compound has the following Structure L-1:

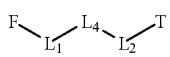

Structure L-1 including stereoisomers and pharmaceutically acceptable salts thereof, wherein:

F is a functional unit of a HPP of a retinoid or retinoid-related compound. Examples of F include Structure F-1 to Structure F-41 as defined supra;

T is a transportational unit of a HPP of a retinoid or retinoid-related compound. For example, T is selected from the group consisting of Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr as defined supra;

$L_1$ is selected from the group consisting of nothing, O, S, —N($L_3$)-, —N($L_3$)-$CH_2$—O, —N($L_3$)-$CH_2$—N($L_5$)-, —O—$CH_2$—O—, —O—CH($L_3$)-O, and —S—CH($L_3$)-O—;

$L_2$ is selected from the group consisting of nothing, O, S, —N($L_3$)-, —N($L_3$)-$CH_2$-O, —N($L_3$)-$CH_2$—N($L_5$)-, —O—$CH_2$—O—, —O—CH($L_3$)-O, —S—CH($L_3$)-O—, —O-$L_3$-, —N-$L_3$-, —S-$L_3$-, —N($L_3$)-$L_5$- and $L_3$;

$L_4$ is selected from the group consisting of nothing, C=O, C=S,

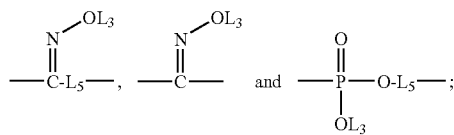

for each $L_1$, $L_2$, and $L_4$, each $L_3$ and $L_5$ is independently selected from the group consisting of nothing, H, $CH_2COOL_6$, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, $NL_3$, or any other pharmaceutically acceptable groups;

$L_6$ is independently selected from the group consisting of H, OH, Cl, F, Br, I, substituted and unsubstituted alkyl, substituted and unsubstituted cycloalkyl, and substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, $P(O)OL_7$, CH=CH, C≡C, $CHL_7$, $CL_5L_7$, aryl, heteroaryl, or cyclic groups; and $L_7$ is independently selected from the group consisting of H, OH, Cl, F, Br, I, substituted and unsubstituted alkyl, substituted and unsubstituted cycloalkyl, and substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, $P(O)OL_6$, CH=CH, C≡C, $CHL_6$, $CL_6L_5$, aryl, heteroaryl, or cyclic groups.

In certain embodiments, a HPP or HPC of a retinoid or retinoid-related compound comprises the structure of Structure L-1, including stereoisomers and pharmaceutically acceptable salts thereof, wherein:

F, $L_1$, $L_2$, and T are defined as supra; and $L_4$ is —C(=O)—.

Examples of HPPs of Retinoids and Retinoid-Related Compounds.

In certain embodiments, a HPP of a retinoid or retinoid-related compound includes a compound having a structure selected from the group consisting of Structure 1, Structure 2, Structure 3, Structure 4, Structure 5, Structure 6, Structure 7, Structure 8, Structure 9, Structure 10, Structure 11, Structure 12, Structure 13, Structure 14, Structure 15, Structure 16, Structure 17, Structure 18, Structure 19, Structure 20, Structure 21, Structure 22, Structure 23, Structure 24, Structure 25, Structure 26, Structure 27, Structure 28, Structure 29, Structure 30, Structure 31, Structure 32, Structure 33, Structure 34, Structure 35, Structure 36, Structure 37, Structure 38, and Structure 39:

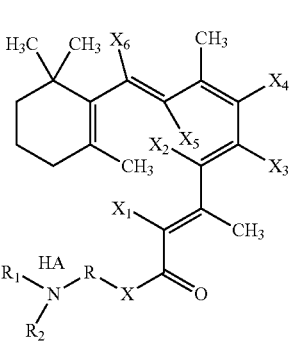

Structure 1

Structure 2
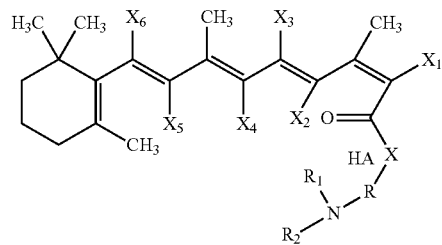
Structure 3
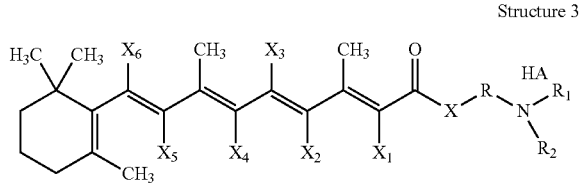
Structure 4
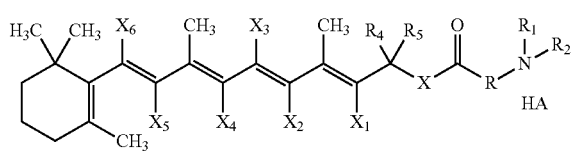
Structure 5
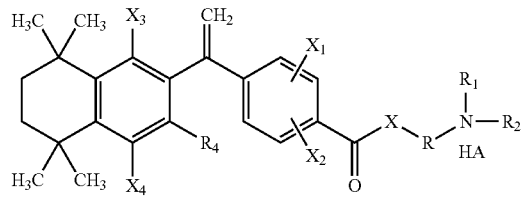
Structure 6
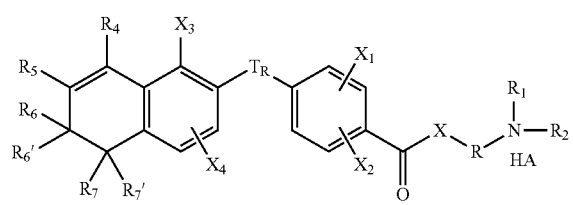
Structure 7
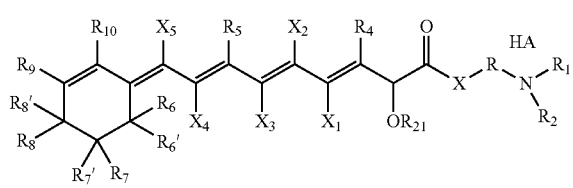
Structure 8
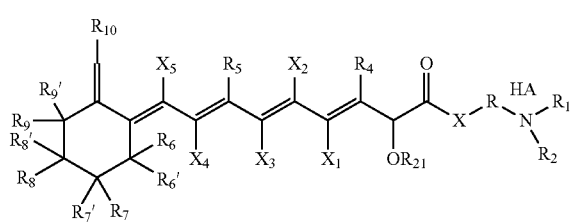
Structure 9
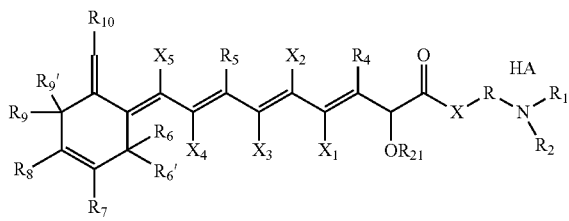
Structure 10
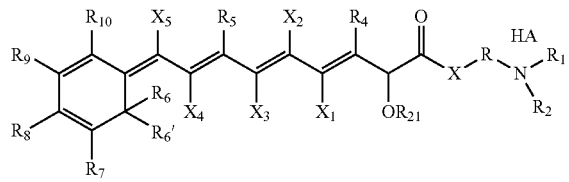
Structure 11
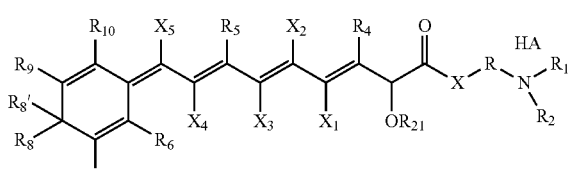
Structure 12
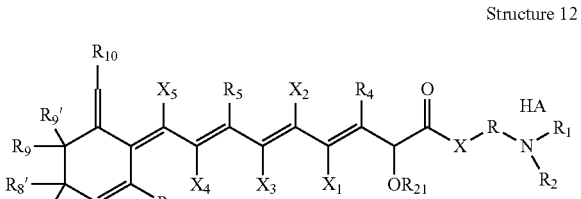
Structure 13
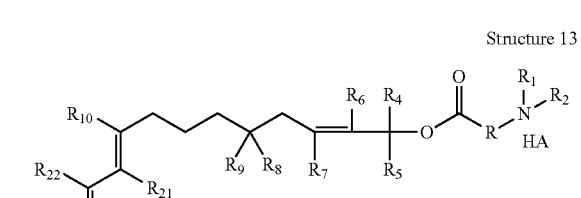
Structure 14
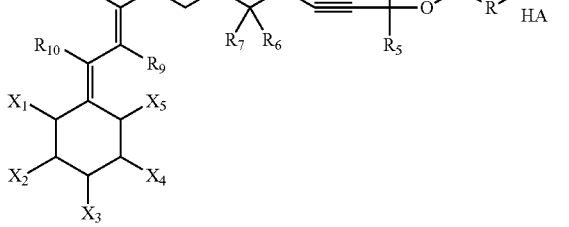

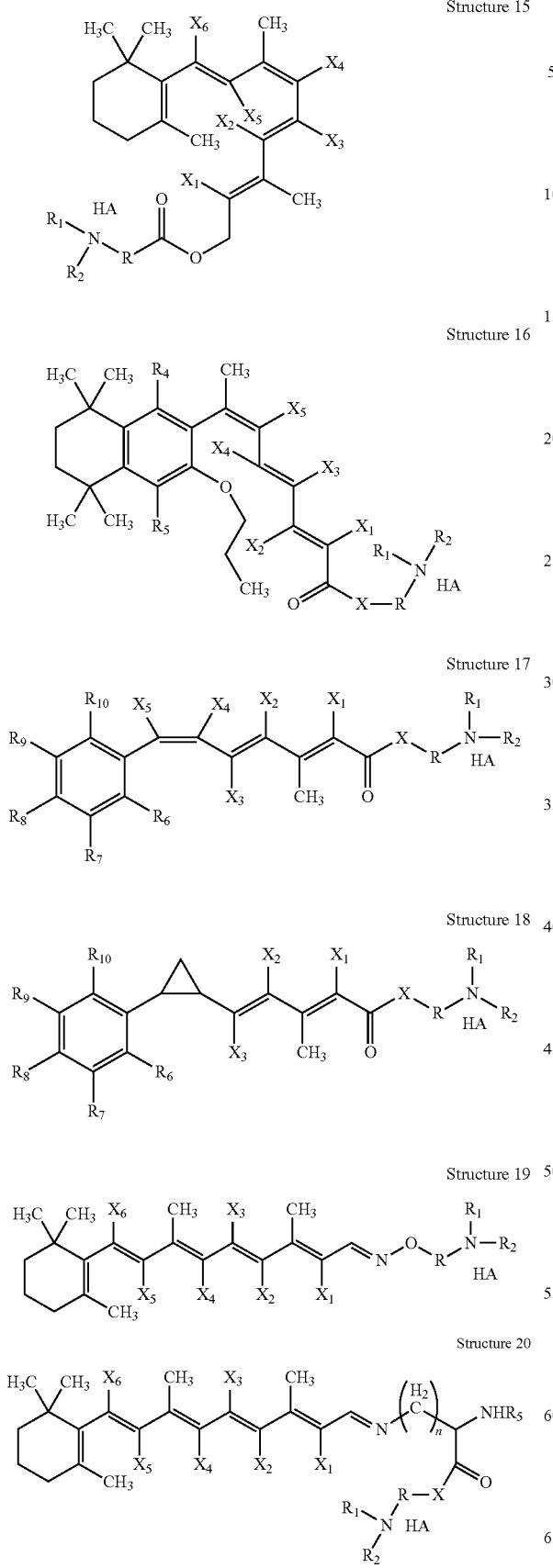
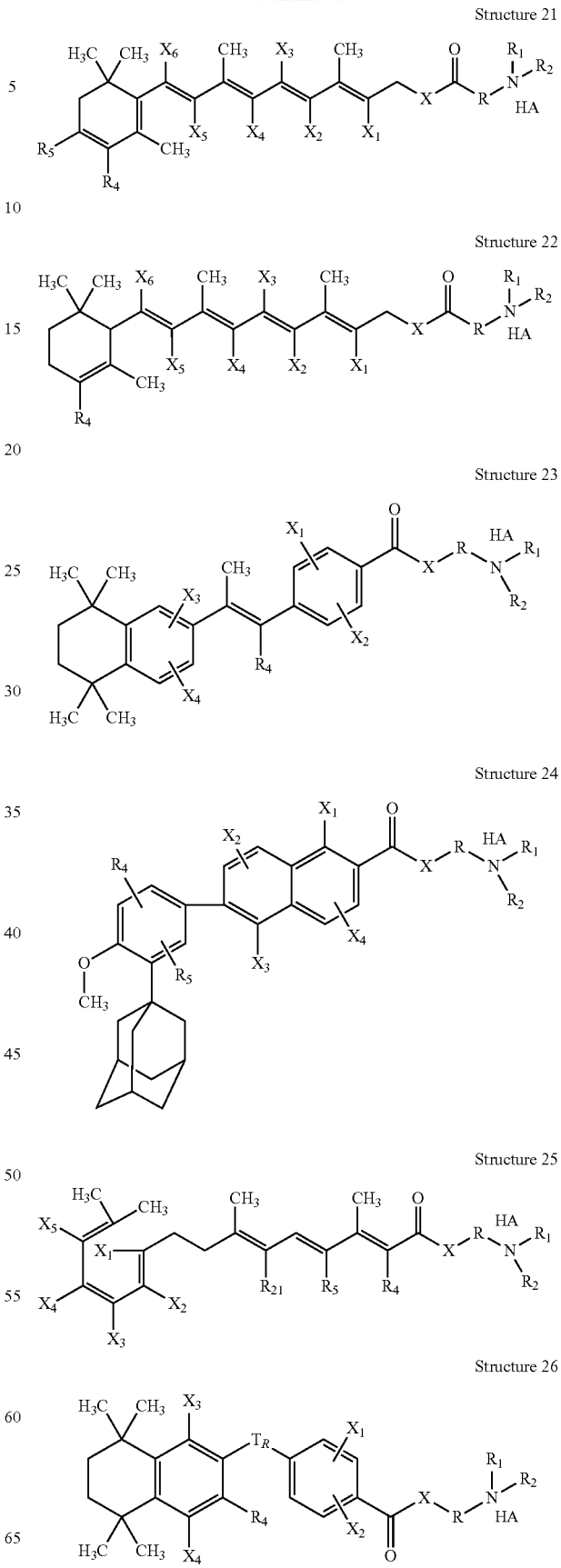

Structure 27
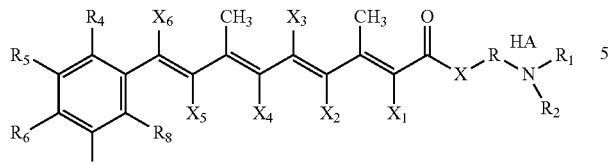
Structure 28
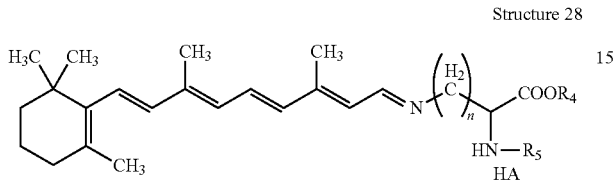
Structure 29
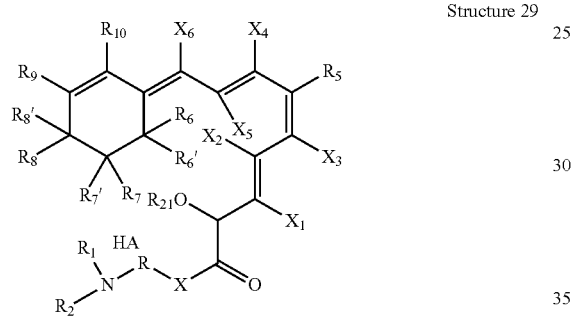
Structure 30
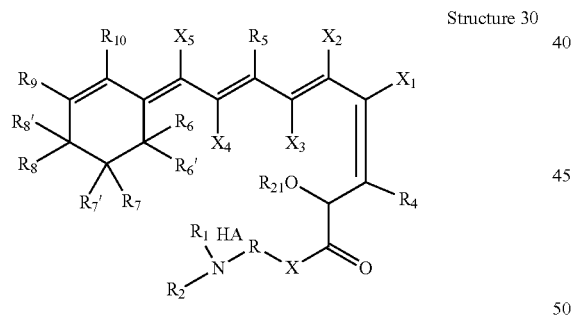
Structure 31
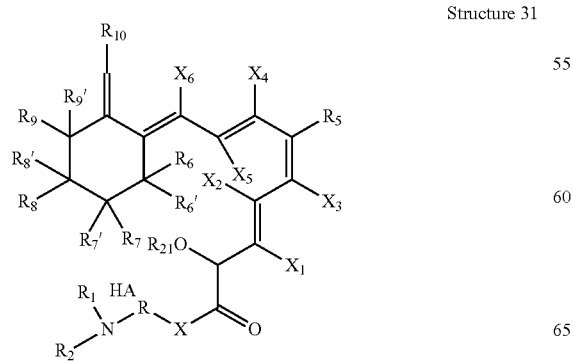
Structure 32
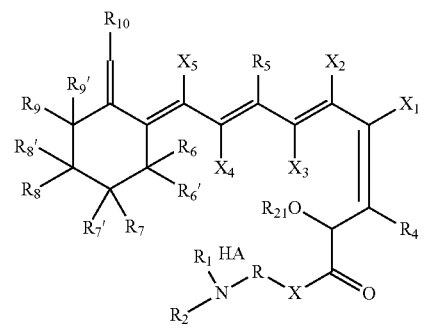
Structure 33
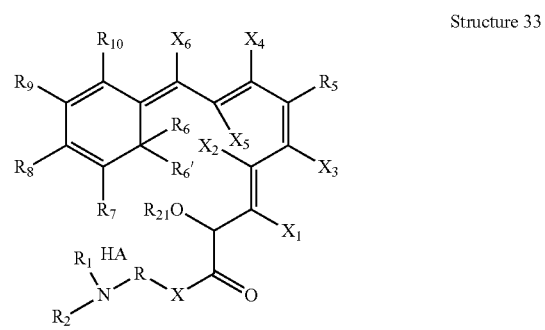
Structure 34
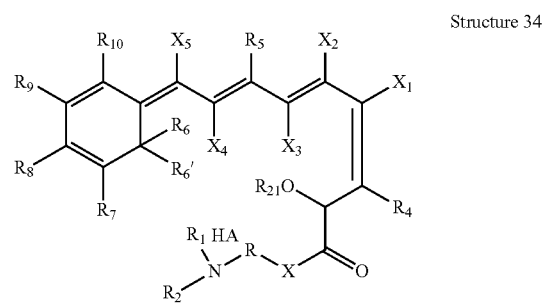
Structure 35
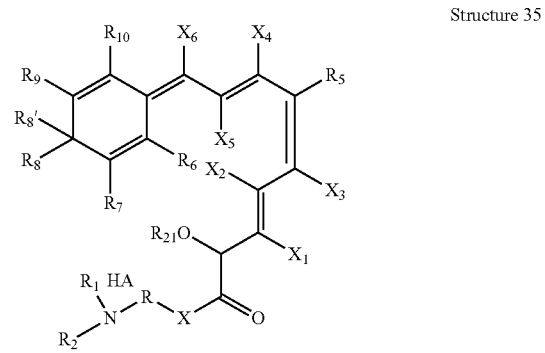
Structure 36
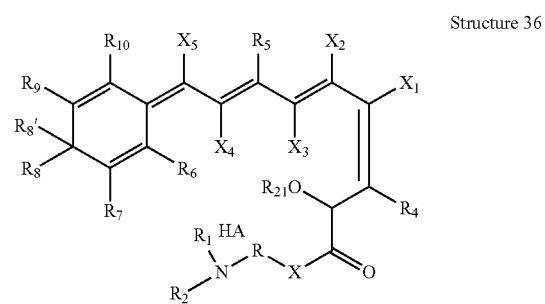

Structure 37

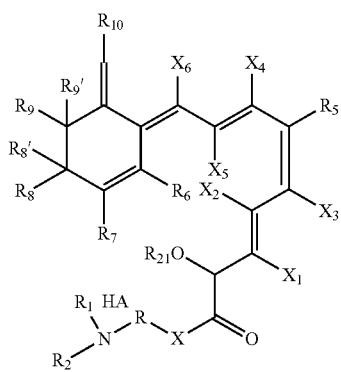

Structure 38

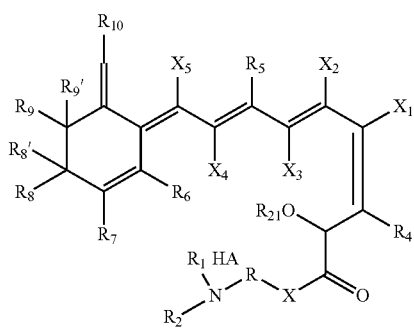

Structure 39

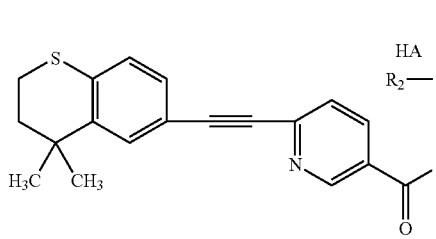

including stereoisomers and pharmaceutically acceptable salts thereof, wherein:

R is selected from the group consisting of nothing, substituted and unsubstituted alkyl, substituted and unsubstituted alkoxyl, substituted and unsubstituted perfluoroalkyl, substituted and unsubstituted alkyl halide, substituted and unsubstituted alkenyl, substituted and unsubstituted alkynyl, substituted and unsubstituted aryl, and substituted and unsubstituted heteroaryl;

$R_1$, $R_2$, $R_4$, $R_5$, $R_6$, $R_6'$, $R_7$, $R_7'$, $R_8$, $R_8'$, $R_9$, $R_9'$, $R_{10}$, $R_{10}'$, $R_{21}$, $R_{22}$, X, $X_1$, $X_2$, $X_3$, $X_4$, $X_5$, $X_6$, $T_R$ and HA are defined the same as supra.

II. Pharmaceutical Compositions Comprising HPPs

Another aspect of the invention relates to a pharmaceutical composition comprising at least one HPP of a retinoid or retinoid-related compound and a pharmaceutically acceptable carrier.

The term "pharmaceutically acceptable carrier" as used herein means a pharmaceutically-acceptable material, composition or vehicle, such as a liquid or solid filler, diluent, excipient, solvent or encapsulating material, involved in carrying or transporting a HPP from one location, body fluid, tissue, organ (interior or exterior), or portion of the body, to another location, body fluid, tissue, organ, or portion of the body.

Each carrier is "pharmaceutically acceptable" in the sense of being compatible with the other ingredients, e.g., a HPP, of the formulation and suitable for use in contact with the tissue or organ of a biological system without excessive toxicity, irritation, allergic response, immunogenicity, or other problems or complications, commensurate with a reasonable benefit/risk ratio.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

In one embodiment, the pharmaceutically acceptable carrier is an aqueous carrier, e.g. buffered saline and the like. In certain embodiments, the pharmaceutically acceptable carrier is a polar solvent, e.g. acetone and alcohol.

The concentration of HPP in these formulations can vary widely, and will be selected primarily based on fluid volumes, viscosities, body weight and the like in accordance with the particular mode of administration selected and the biological system's needs. For example, the concentration can be 0.0001% to 100%, 0.001% to 50%, 0.01% to 30%, 0.1% to 10% wt.

The compositions of the invention can be administered for prophylactic, therapeutic, and/or hygienic use. Such administration can be topical, mucosal, e.g., oral, nasal, vaginal, rectal, parenteral, transdermal, subcutaneous, intramuscular, intravenous, via inhalation, ophthalmic and other convenient routes. The pharmaceutical compositions can be administered in a variety of unit dosage forms depending upon the method of administration. For example, unit dosage forms suitable for oral administration include powder, tablets, pills, capsules and lozenges.

Thus, a typical pharmaceutical composition for intravenous administration would be about $10^{-10}$ g to about 100 g, about $10^{-10}$ g to about $10^{-3}$ g, about $10^{-9}$ g to about $10^{-6}$ g, about $10^{-6}$ g to about 100 g, about 0.001 g to about 100 g, about 0.01 g to about 10 g, or about 0.01 g to about 1 g per subject per day. Dosages from about 0.01 mg, up to about 5 g, per subject per day may be used. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

III. Applications of HPPs i) Methods for Penetrating a Biological Barrier.

Another aspect of the invention relates to a method of using a composition of the invention in penetrating one or more biological barriers in a biological subject. The method comprises a step of administering to a biological subject a HPP or a retinoid or retinoid-related compound, or a pharmaceutical composition thereof. In certain embodiments, a HPP exhibits more than about 20 times or higher, 50 times or higher, >about 100 times or higher, >about 200 time higher, >about 300 times or higher, >about 500 times or higher, >about 1,000 times or higher penetration rate through one or more biological barriers than its parent drug.

The term "biological barrier" as used herein refers to a biological layer that separates an environment into different spatial areas or compartments, which separation is capable of modulating (e.g. restricting, limiting, enhancing or taking no action in) the passing through, penetrating or translocation of substance or matter from one compartment/area to another. The different spatial areas or compartments as referred to herein may have the same or different chemical or biological environment(s). The biological layer as referred herein includes, but is not limited to, a biological membrane, a cell layer, a biological structure, an inner surface of subjects, organisms, organs or body cavities, an external surface of subjects, organisms, organs or body cavities, or any combination or plurality thereof.

Examples of a biological membrane include a lipid bilayer structure, eukaryotic cell membrane, prokaryotic cell membrane, and intracellular membrane (e.g., nucleus or organelle membrane, such as membrane or envelope of Golgi apparatus, rough and smooth endoplasmic reticulum (ER), ribosomes, vacuoles, vesicles, liposomes, mitochondria, lysosome, nucleus, chloroplasts, plastids, peroxisomes or microbodies).

The lipid bilayer referred to herein is a double layer of lipid-class molecules, including, but not limited to, phospholipids and cholesterol. In a particular embodiment, lipids for bilayer are amphiphilic molecules consisting of polar head groups and non-polar fatty acid tails. The bilayer is composed of two layers of lipids arranged so that their hydrocarbon tails face one another to form an oily core held together by the hydrophobic effect, while their charged heads face the aqueous solutions on either side of the membrane. In another particular embodiment, the lipid bilayer may contain one or more embedded protein and/or sugar molecule(s).

Examples of a cell layer include a lining of eukaryotic cells (e.g., epithelium, lamina propria and smooth muscle or muscularis mucosa (in gastrointestinal tract)), a lining of prokaryotic cells (e.g., surface layer or S-layer which refers to a two dimensional structure monomolecular layer composed of identical proteins or glycoproteins, specifically, an S-layer refers to a part of a cell envelope commonly found in bacteria and archaea), a biofilm (a structured community of microorganisms encapsulated within a self-developed polymeric matrix and adherent to a living or inert surface), and a plant cell layer (e.g., epidermis). The cells may be normal cells or pathological cells (e.g. disease cells, cancer cells).

Examples of biological structures include structures sealed by tight or occluding junctions which provide a barrier to the entry of toxins, bacteria and viruses, e.g. the blood milk barrier and the blood brain barrier (BBB). In particular, BBB is composed of an impermeable class of endothelium, which presents both a physical barrier through tight junctions adjoining neighboring endothelial cells and a transport barrier comprised of efflux transporters. The biological structure may also include a mixture of cells, proteins and sugars (e.g. blood clots).

Examples of the inner surface of subjects, organisms, organs or body cavities include buccal mucosa, esophageal mucosa, gastric mucosa, intestinal mucosa, olfactory mucosa, oral mucosa, bronchial mucosa, uterine mucosa and endometrium (the mucosa of the uterus, inner layer of the wall of a pollen grain or the inner wall layer of a spore), or a combination or plurality thereof.

Examples of the external surface of subjects, organisms, organs or body cavities include capillaries (e.g. capillaries in the heart tissue), mucous membranes that are continuous with skin (e.g. such as at the nostrils, the lips, the ears, the genital area, and the anus), outer surface of an organ (e.g. liver, lung, stomach, brain, kidney, heart, ear, eye, nose, mouth, tongue, colon, pancreas, gallbladder, duodenum, rectum stomach, colonrectum, intestine, vein, respiratory system, vascular, the anorectum and pruritus ani), skin, cuticle (e.g. dead layers of epidermal cells or keratinocytes or superficial layer of overlapping cells covering the hair shaft of an animal, a multilayered structure outside the epidermis of many invertebrates, plant cuticles or polymers cutin and/or cutan), external layer of the wall of a pollen grain or the external wall layer of a spore), and a combination or plurality thereof.

In addition, a biological barrier further includes a sugar layer, a protein layer or any other biological layer, or a combination or plurality thereof. For example, skin is a biological barrier that has a plurality of biological layers. A skin comprises an epidermis layer (outer surface), a demis layer and a subcutaneous layer. The epidermis layer contains several layers including a basal cell layer, a spinous cell layer, a granular cell layer, and a stratum corneum. The cells in the epidermis are called keratinocytes. The stratum corneum ("horny layer") is the outmost layer of the epidermis, wherein cells here are flat and scale-like ("squamous") in shape. These cells contain a lot of keratin and are arranged in overlapping layers that impart a tough and oilproof and waterproof character to the skin's surface.

ii) Methods for Diagnosing a Condition in a Biological System.

Another aspect of the invention relates to a method of using a composition of the invention in diagnosing a condition in a biological system. The method comprises the following steps:

1) administering a composition comprising a HPP of a retinoid or retinoid-related compound to the biological subject;

2) detecting the presence, location or amount of the HPP, the functional unit of the HPP or a metabolite thereof in the biological subject; and 3) determining a condition in the biological system.

In certain embodiments, the HPP (or the agent cleaved from the HPP) aggregates in the site of action where a condition occurs. In certain embodiments, the presence, location or amount of the functional unit of the HPP is also detected. In certain embodiments, the onset, development, progress, or remission of a condition (e.g., tumor) associated is also determined.

In certain embodiments, the HPP is labeled with or conjugated to a detectable agent. Alternatively, the HPP is prepared to include radioisotopes for detection. Numerous detectable agents are available which can be generally grouped into the following categories:

(a) Radioisotopes, such as $^{35}S$, $^{14}C$, $^{13}C$, $^{15}N$, $^{125}I$, $^{3}H$, and $^{131}I$. The diagnostic agent can be labeled with the radioisotope using the techniques known in the art and radioactivity can be measured using scintillation counting; in addition, the diagnostic agent can be spin labeled for electron paramagnetic resonance for carbon and nitrogen labeling.

(b) Fluorescent agents such as BODIPY, BODIPY analogs, rare earth chelates (europium chelates), fluorescein and its derivatives, FITC, 5,6 carboxyfluorescein, rhodamine and its derivatives, dansyl, Lissamine, phycoerythrin, green fluorescent protein, yellow fluorescent protein, red fluorescent protein and Texas Red. Fluorescence can be quantified using a fluorometer.

(c) Various enzyme-substrate agents, such luciferases (e.g., firefly luciferase and bacterial luciferase), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of enzyme-substrate combinations include, for example: (i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB)); (ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

In certain embodiments, the detectable agent is not necessarily conjugated to the diagnostic agent but is capable of recognizing the presence of the diagnostic agent and the diagnostic agent can be detected.

In certain embodiments, the HPP of the invention can be provided in a kit, i.e., a packaged combination of reagents in predetermined amounts with instructions for performing the diagnostic assay. Where the HPP is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

iii) Methods for Screening a Substance for a Desired Character

Another aspect of the invention relates to a method of screening a HPP for a desired character.

In certain embodiments, the method comprises:
1) covalently linking a test functional unit to a transportational unit through a linker to form a test composition (or covalently linking a functional unit to a test transportational unit through a linker, or covalently linking a functional unit to a transportational unit through a test linker)
2) administering the test composition to a biological system; and
3) determining whether the test composition has the desired nature or character.

In one embodiment, a desired character may include, for example, 1) the ability of a test functional unit to form a high penetration composition or convert back to a parent drug, 2) the penetration ability and/or rate of a test composition, 3) the efficiency and/or efficacy of a test composition, 4) the transportational ability of a test transportational unit, and 5) the cleavability of a test linker.

iv) Methods for Treating a Condition in a Biological Subject

Another aspect of the invention relates to a method of using a composition of the invention in treating a condition in a biological system. The method comprises administering the pharmaceutical composition to the biological system.

The term "treating" as used herein means curing, alleviating, inhibiting, or preventing. The term "treat" as used herein means cure, alleviate, inhibit, or prevent. The term "treatment" as used herein means cure, alleviation, inhibition or prevention.

The term "biological system," "biological subject" or "subject" as used herein means an organ, a group of organs that work together to perform a certain task, an organism, or a group of organisms. The term "organism" as used herein means an assembly of molecules that function as a more or less stable whole and has the properties of life, such as animal, plant, fungus, or micro-organism.

The term "animal" as used herein means an eukaryotic organism characterized by voluntary movement. Examples of animal include, without limitation, vertebrata (e.g. human, mammals, birds, reptiles, amphibians, fishes, marsipobranchiata and leptocardia), tunicata (e.g. thaliacea, appendicularia, sorberacea and ascidioidea), articulata (e.g. insecta, myriapoda, malacapoda, arachnida, pycnogonida, merostomata, crustacea and annelida), gehyrea (anarthropoda), and helminthes (e.g. rotifera).

The term "plant" as used herein means organisms belonging to the kingdom Plantae. Examples of plant include, without limitation, seed plants, bryophytes, ferns and fern allies. Examples of seed plants include, without limitation, cycads, ginkgo, conifers, gnetophytes, angiosperms. Examples of bryophytes include, without limitation, liverworts, hornworts and mosses. Examples of ferns include, without limitation, ophioglossales (e.g. adders-tongues, moonworts, and grape-ferns), marattiaceae and leptosporangiate ferns. Examples of fern allies include, without limitation, lycopsida (e.g. club-mosses, spikemosses and quillworts), psilotaceae (e.g. lycopodiophyta and whisk ferns) and equisetaceae (e.g. horsetails).

The term "fungus" as used herein means a eukaryotic organism that is a member of the kingdom Fungi. Examples of fungus include, without limitation, chytrids, blastocladiomycota, neocallimastigomycota, zygomycota, glomeromycota, ascomycota and basidiomycota.

The term "micro-organism" as used herein means an organism that is microscopic (e.g. with length scale of micrometer). Examples of micro-organism include, without limitation, bacteria, fungi, archaea, protists and microscopic plants (e.g. green algae) and microscopic animals (e.g. plankton, planarian and amoeba).

Some examples of the conditions the method can treat include conditions that can be treated by the parent drug of the HPP.

v). Methods of Using HPPs of Retinoids and Retinoid-Related Compounds and Pharmaceutical Compositions Thereof in Treatments.

Another aspect of the invention relates to a method of using HPPs of retinoids or retinoid-related compounds, or pharmaceutical compositions thereof in treating a condition in a biological system or subject by administering a HPP of a retinoid or retinoid-related compound, or a pharmaceutical composition thereof to the biological system or subject.

Retinoids and retinoid-related compounds can be used to regulate a wide range of biological processes in a biological system. Conditions that are related to such biological processes are treatable by the corresponding retinoids or retinoid-related compounds, and therefore treatable by HPPs/HPCs of the retinoids/retinoid-related compounds, and a pharmaceutical composition thereof.

Without being bounded by any theory, it is believed that Vitamin A (retinol) and retinal are in chemical equilibrium in the body and equivalent antixerophthalmic acitivity. Examples of conditions that are related to Vitamin A deficiency include, without limitation, nyctalopia, keratomalacia, keratinization, dry skin, lowered resistance to infection, decreased growth rate, slow bone development, thickening of bone, diminished production of cortical steroids, and fetal malformations.

Without being bounded by any theory, it is believed that tretinoin (all-trans-retinoic acid) decreases cohesiveness of follicular epithelial cells with decreased microcomedo formation and stimulates mitotic activity increased turnover of follicular epithelial cells causing extrusion of the comedones. Tretinoin has been used in the treatment of acne vulgaris, photoaging, hyperpigmented macules (liver spot) and premature wrinkles, drug-induced photosensitivity, psoriasis, epidermal wound healing, xerophthalmia, keloids, hyperkeratotic skin disease.

Without being bounded by any theory, it is believed that isotretinoin inhibits sebaceous gland function and keratinization. Isotretinoin is indicated for the treatment of severe recalcitrant cystic acne, basal cell carcinoma, cervical cancer, mycosis fungoides (cutaneous T-cell lymphoma), Darier's disease, lamellar ichthyosis, pityriasis rubra pilaris, herpes simplex infections, Grover's disease, lichen planus, refractory rosacea, keratosis palmaris et plantaris, leukoplakia, squamous cell skin cancer, and xeroderma pigmentosum.

Without being bounded by any theory, it is believed that alitretinoin (9-cis-retinoic acid) is a naturally-occurring endogenous retinoid that binds to and activates all known intracellular retinoid receptor subtypes (RAR, RAR, RAR, RXR, RXR, and RXR). Once activated these receptors function as transcription factors that regulate the expression of genes that control the process of cellular differentiation and proliferation in both normal and neoplastic cells. Alitretinoin inhibits the growth of Kaposi's sarcoma (KS) cells in vitro. Alitretinoin is used for the treatment of Kaposi's sarcoma and myelodysplastic syndromes.

Targretin oral formulation is used for the treatment of cutaneous T-cell lymphoma (CTCL), head and neck carcinoma, systemic Kaposi's sarcoma, lung cancer, ovarian cancer, prostate cancer, and renal cell cancer.

Retiferol derivatives are used for the treatment of hyperproliferative skin diseases such as psoriasis, basal cell carcinomas, disorders of keratinization and keratosis, neoplastic diseases, disorders of the sebaceous glands such as acne and seborrhoic dermatitis, the conditions associated with photodamage, the skin damaged through sun exposure, the effects of wrinkling, elastosis and premature ageing (Hilpert, et al., U.S. Pat. No. 6,437,142).

Adapalene is used for the topical treatment of acne vulgaris.

Acyclic retinoids are used for prevention of second primary tumors (Yasutoshi Muto, et al., the New England Journal of Medicine, 340, 1046 (1999)).

(E, E, E)-7-(2-n-propoxy-5,5,8,8-tetramethyl-5,6,7,8-tetrahydro-naphthalen-3-yl)-6-fluoro-3-methylocta-2,4,6-trienoic acid may be used for the treatment of type 2 diabetes and other metabolic disorders (Deng T, et al., Biol. Pharm. Bull. 28(7), 1192, 2005).

Various retinoids and retinoid-related compounds have been synthesized and show retinoid activities. (U.S. Pat. Nos. 5,648,563; 5,648,385; 5,618,839; 5,559,248; 5,616,712; 5,616,597; 5,602,135; 5,599,819; 5,556,996; 5,534,516; 5,516,904; 5,498,755; 5,470,999; 5,468,879; 5,455,265; 5,451,605; 5,426,118; 5,407,937; 5,399,586; 5,399,561; 5,391,753). Numerous experimental retinoids compounds, for example, 4-[1-(5,6,7,8-tetrahydro-3,5,5,8,8-pentamethyl-2-naphthalenyl)ethenyl]benzoic acid (bexaroten, Targretin®), are used for the treatment of cancers and other diseases.

Conditions that are treatable by retinoids or retinoid-related compounds include, but are not limited to, Vitamin A deficiency conditions, infection-related conditions, skin conditions, eye conditions, bone conditions, tumor and related conditions, hair loss, and metabolic disorders (e.g. diabetes such as type 2 diabetes).

Vitamin A deficiency related conditions include, for example, nyctalopia, keratomalacia, keratinization, dry skin, lowered resistance to infection, decreased growth rate, slow bone development, thickening of bone, diminished production of cortical steroids, and fetal malformations.

Examples of skin conditions include, without limitation, keratinization, dry skin, skin damage through sun exposure (e.g. photoaging), hyperpigmented macules (liver spot), wrinkles, elastosis and premature aging (e.g. wrinkles), drug-induced photosensitivity, diminished production of cortical steroids, epidermal wound healing, keloids, hyperkeratotic skin disease, Darier's disease, lamellar ichthyosis, pityriasis rubra pilaris, lichen planus, refractory rosacea, keratosis palmaris et plantaris, leukoplakia, xeroderma pigmentosum, Kaposi's sarcoma, AIDS-related Kaposi's sarcoma, systemic Kaposi's sarcoma, cutaneous T-cell lymphoma (CTCL, e.g. mycosis fungoides), hyperproliferative skin diseases (e.g. psoriasis, basal cell carcinomas), disorders of keratinization and keratosis, neoplastic diseases, disorders of the sebaceous glands (e.g. acne vulgaris, recalcitrant cystic acne, acne and seborrhoic dermatitis).

Infection-related conditions include, without limitation, herpes simplex infections and lowered resistance to infections.

Examples of eye conditions include, without limitation, nyctalopia, keratinization, xerophthalmia and Grover's disease.

Examples of bone conditions include, without limitation, bone thickening and myelodysplastic syndromes.

Examples of tumor and related conditions include, without limitation, benign tumor, breast cancer, colon-rectum cancer, lung or other respiratory system cancers, skin cancer, basal cell carcinoma, cervical cancer, mycosis fungoides, Kaposi's sarcoma, AIDS-related Kaposi's sarcoma, systemic Kaposi's sarcoma, cutaneous T-cell lymphoma (CTCL), squamous cell skin cancer, second primary tumors, head and neck carcinoma, ovarian cancer, prostate cancer, and renal cell cancer.

Some examples of the conditions that are treatable by a method comprising using a HPP/HPC of a retinoid or retinoid-related compound, or a pharmaceutical composition thereof include, without limitation, Vitamin A deficiency related conditions, infection-related conditions, skin conditions, eye conditions, bone conditions, tumor and related conditions, and metabolic disorders (e.g. diabetes such as type 2 diabetes).

In certain embodiments, a method of treating a retinoid treatable condition condition comprises administering to a biological system a HPP/HPC of a retinoid or a retinoid related compound such as retinol (vitamin A), retinal, retiferol, tretinoin (all-trans-retinoic acid, e.g. retinoic acid, Retin-A), isotretinoin, alitretinoin (9-cis-retinoic acid), etretinate, acitretin, tazarotene, bexarotene and Adapalene, a compound having a structure selected from the group consisting of Structure R1, Structure R2, Structure R3, Structure R4, Structure R5, Structure R6, Structure R7, Structure R8, Structure R9, Structure R10, Structure R11, Structure R12, Structure R13, Structure R14, Structure R15, Structure R16, Structure R17, Structure R18, Structure R19, Structure R20, Structure R21, Structure R22, Structure R23, Structure R24, Structure R25, Structure R26, Structure R27, Structure R28, Structure R29, Structure R30, Structure R31, Structure R32, Structure R33, Structure R34, Structure R35, Structure R36, Structure R37, Structure R38, and Structure R39 as defined supra, and mimics thereof.

In certain embodiments, a method of treating a Vitamin A deficiency related condition comprises administering to a biological system a HPP/HPC of a retinoid or a retinoid related compound, or a pharmaceutical composition thereof. In a biological system, retinoid regulates a wide range of processes such as vision, reproduction, metabolism, differentiation, bone development, and pattern formation during embryogenesis. Vitamin A (retinol) and retinal are in chemical equilibrium in the body and equivalent antixerophthalmic acitivity. Examples of Vitamin A deficiency related conditions include, without limitation, nyctalopia, keratomalacia, keratinization, dry skin, lowered resistance to infection, decreased growth rate, slow bone development, thickening of bone, diminished production of cortical steroids, and fetal malformations.

In certain embodiments, a method of treating a skin condition comprises administering to a biological system a HPP/HPC of a retinoid or retinoid-related compound (e.g. tretinoin, isotretinoin, alitretinoin, targretin, retiferol derivatives, and adapalene), or a pharmaceutical composition thereof. Tretinoin (all-trans-retinoic acid) decreases cohesiveness of follicular epithelial cells with decreased microcomedo formation and stimulates mitotic activity increased turnover of follicular epithelial cells causing extrusion of the comedones. Isotretinoin inhibits sebaceous gland function and keratinization.

In certain embodiments, a method of treating a infection-related conditions comprises administering to a biological system a HPP/HPC of a retinoids or a retinoid-related compound (e.g. isotretinoin), or a pharmaceutical composition thereof.

In certain embodiments, a method of treating a bone condition comprises administering to a biological system a HPP/HPC of a retinoids or a retinoid-related compound (e.g. alitretinoin), or a pharmaceutical composition thereof.

In certain embodiments, a method of treating a tumor and related conditions comprises administering to a biological system a HPP/HPC of a retinoids or a retinoid-related compound (e.g. isotretinoin, targretin, bexaroten, Targretin®, acyclic retinoids), or a pharmaceutical composition thereof.

In certain embodiments, a method of treating a condition in a subject amelioratable or treatable with retinoids or retinoid-related compounds comprises administering a therapeutic effective amount of a HPP of a retinoid or retinoid-related compound, or a pharmaceutical composition thereof to the subject.

A HPP or a pharmaceutical composition thereof can be administered to a biological system by any administration route known in the art, including without limitation, oral, enteral, buccal, nasal, topical, rectal, vaginal, aerosol, transmucosal, epidermal, transdermal, dermal, ophthalmic, pulmonary, subcutaneous, and/or parenteral administration. The pharmaceutical compositions can be administered in a variety of unit dosage forms depending upon the method of administration.

A parenteral administration refers to an administration route that typically relates to injection which includes but is not limited to intravenous, intramuscular, intraarterial, intrathecal, intracapsular, intraorbital, intra cardiac, intradermal, intraperitoneal, transtracheal, subcutaneous, subcuticular, intraarticular, subcapsular, subarachnoid, intraspinal, and/or intrasternal injection and/or infusion.

A HPP or a pharmaceutical composition thereof can be given to a subject in the form of formulations or preparations suitable for each administration route. The formulations useful in the methods of the invention include one or more HPPs, one or more pharmaceutically acceptable carriers therefor, and optionally other therapeutic ingredients. The formulations may conveniently be presented in unit dosage form and may be prepared by any methods well known in the art of pharmacy. The amount of active ingredient which can be combined with a carrier material to produce a single dosage form will vary depending upon the subject being treated and the particular mode of administration. The amount of a HPP which can be combined with a carrier material to produce a pharmaceutically effective dose will generally be that amount of a HPP which produces a therapeutic effect. In certain embodiments, out of one hundred percent, the amount of HPP/HPC ranges from about 0.01 percent to about ninety-nine percent of the HPP. In certain embodiments, the amount of HPP/HPC ranges from about 0.1 percent to about 20 percent. In certain embodiments, the amount of HPP/HPC rangesfrin about 1 percent to about 5 percent.

Methods of preparing these formulations or compositions include the step of bringing into association a HPP with one or more pharmaceutically acceptable carriers and, optionally, one or more accessory ingredients. In general, the formulations are prepared by uniformly and intimately bringing into association a HPP with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a HPP as an active ingredient. A compound may also be administered as a bolus, electuary, or paste.

In solid dosage forms for oral administration (e.g., capsules, tablets, pills, dragees, powders, granules and the like), the HPP is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate, (5) solution retarding agents, such as paraffin, (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered retinoids or peptidomimetic moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of a HPP therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain pacifying agents and may be of a composition that they release the HPP(s) only, or preferentially, in a certain portion of the gastrointestinal tract, optionally, in a delayed manner. Examples of embedding compositions which can be used include polymeric substances and waxes. The HPP can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the HPP, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the HPP, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more HPPs with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent. Formulations which are suitable for vaginal administration also include pessaries, tampons, creams, gels, pastes, foams or spray formulations containing such carriers as are known in the art to be appropriate.

Formulations for the topical or transdermal or epidermal or dermal administration of a HPP composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required. The ointments, pastes, creams and gels may contain, in addition to the HPP composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the HPP composition, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

A HPP or a pharmaceutical composition thereof can be alternatively administered by aerosol. This can be accomplished by preparing an aqueous aerosol, liposomal preparation or solid particles containing the HPPs. A nonaqueous (e.g., fluorocarbon propellant) suspension could be used. Sonic nebulizers can also be used. An aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches can also be used to deliver HPP compositions to a tumor site. Such formulations can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Formulations suitable for parenteral administration comprise a HPP in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacterostats, solutes which render the formulation isotonic with the blood of the intended recipient or suspending or thickening agents.

Examples of suitable aqueous and nonaqueous carriers which may be employed in the formulations suitable for parenteral administration include water, ethanol, polyols (e.g., such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Formulations suitable for parenteral administration may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Injectable depot forms are made by forming microencapsule matrices of a HPP or in biodegradable polymers such as polylactide-polyglycolide. Depending on the ratio of the HPP to polymer, and the nature of the particular polymer employed, the rate of drug release can be controlled. Examples of other biodegradable polymers include poly (orthoesters) and poly(anhydrides). Depot injectable formulations are also prepared by entrapping the HPP in liposomes or microemulsions which are compatible with body tissue.

In certain embodiments, a HPP of a retinoid or retinoid-related compound, or a pharmaceutical composition thereof is delivered to a disease or tumor site in a therapeutically effective dose. As is known in the art of pharmacology, the precise amount of the pharmaceutically effective dose of a HPP that will yield the most effective results in terms of efficacy of treatment in a given patient will depend upon, for example, the activity, the particular nature, pharmacokinetics, pharmacodynamics, and bioavailability of a particular HPP, physiological condition of the subject (including race, age, sex, weight, diet, disease type and stage, general physical condition, responsiveness to a given dosage and type of medication), the nature of pharmaceutically acceptable carriers in a formulation, the route and frequency of administration being used, and the severity or propensity of a disease caused by pathogenic target microbial organisms, to name a few. However, the above guidelines can be used as the basis for fine-tuning the treatment, e.g., determining the optimum dose of administration, which will require no more than routine experimentation consisting of monitoring the subject and adjusting the dosage. Remington: The Science and Practice of Pharmacy (Gennaro ed. 20.sup.th edition, Williams & Wilkins PA, USA) (2000).

IV. Advantages

Retinoids and related compounds are often too lipophilic and penetrate the skin membrane barrier very slowly. When retinoids are taken orally, retinoids and related compounds are rapidly metabolized by enzymes. In the case of injection, administration of retinoids is painful and in many cases requires frequent and costly office visits to treat chronic conditions.

In certain embodiments, since a HPP of the invention is capable of crossing one or more biological barriers, the HPP can be administered locally (e.g., topically or transdermally) to reach a location where a condition occurs without the necessity of a systematic administration (e.g., oral or parenteral administration). A local administration and penetration of a HPP allows the HPP to reach the same level of local concentration of an agent or drug with much less amount or dosage of HPP in comparison to a systematic administration of a parent agent or drug; alternatively, a higher level of local concentration which may not be afforded in the systematic administration, or if possible, requires significantly higher dosage of an agent in the systematic administration. The high local concentration of the HPP or its parent agent if being cleaved enables the treatment of a condition more effectively or much faster than a systematically delivered parent agent and the treatment of new conditions that may not be possible or observed before. The local administration of the HPP may allow a biological subject to reduce potential sufferings from a systemic administration, e.g., adverse reactions associated with the systematic exposure to the agent, gastrointestinal/renal effects. Additionally, the local administration may allow the HPP to cross a plurality of biological barriers and reach systematically through, for example, general circulation and thus avoid the needs for systematic administration (e.g., injection) and obviate the pain associated with the parenteral injection.

In certain embodiments, a HPP or a pharmaceutical composition according to the invention can be administered systematically (e.g., orally or parenterally). The HPP or the active agent (e.g., drug or metabolite) of the HPP may enter the general circulation with a faster rate than the parent agent and gain faster access to the action site a condition. Additionally, the HPP can cross a biological barrier (e.g., blood brain barrier) which has not been penetrated if a parent agent is administered alone and thus offer novel treatment of conditions that may not be possible or observed before.

For example, HPPs of retinoids or retinoid-related compounds in the invention demonstrated high penetration rate through a biological barrier (e.g., >about 10 times, >about 50 times, >about 100 times, >about 200 times, >about 300 times, >about 1000 times higher than if the retinoids or retinoid-related compounds are administered alone). No or few adverse side effect was observed from the subjects that took retinoids HPP, while side effects (such as nausea, hair loss, and increased susceptibility to infection) were observed from the subjects that took the parent retinoids at the similar dosage.

V. EXAMPLES

The following examples are provided to better illustrate the claimed invention and are not to be interpreted in any way as limiting the scope of the invention. All specific compositions, materials, and methods described below, in whole or in part, fall within the scope of the invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention.

Example 1

Preparation of a HPP from a Parent Drug

Preparation of a HPP from a Parent Drug which Contains at Least One Carboxylic group.

In certain embodiments, a parent compound having Structure F—C:

Structure F-C

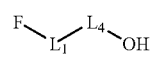

is converted to a HPP having Structure L-1:

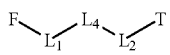

Structure L-1 including stereoisomers and pharmaceutically acceptable salts thereof, wherein:

F, $L_1$, $L_2$, and $L_4$ are defined as supra;

T is a transportational unit of a HPP of a retinoid or retinoid-related compound. For example, T is selected from the group consisting of Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr as defined supra; and In certain embodiments of the invention, a HPP having Structure L-1 is prepared according to organic synthesis by reacting the parent compounds or derivatives of the parent compounds having Structure D (e.g. acid halides, mixed anhydrides of the parent compounds, etc.):

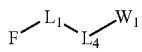

Structure D with compounds of Structure E (Scheme 1):

T-$L_2$-H

Structure E wherein $W_1$ is selected from the group consisting of OH, halogen, alkoxycarbonyl and substituted aryloxycarbonyloxy; and F, $L_1$, $L_2$, $L_4$, and T are defined as supra.

Scheme 1. Preparation of a HPP from a parent compound (I).

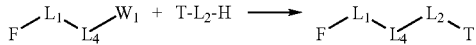

In certain embodiments of the invention, a HPP having Structure L-1 is prepared according to organic synthesis by reacting a salt of parent compounds or derivatives of the parent compounds having Structure G (e.g. sodium salt, potassium salt, triethylamine salt, or polymer bond organic or inorganic base salt, etc.):

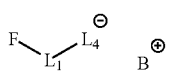

Structure G with compounds of Structure H (Scheme 2):

T-$L_2$-$W_2$.HA

Structure H wherein $W_2$ is selected from the group consisting of p-toluenesulphonyl, halogen, alkoxycarbonyl and substituted aryloxycarbonyloxy; and F, $L_1$, $L_2$, $L_4$, and T are defined the same as supra.

Scheme 2. Preparation of a HPP from a parent compound (II).

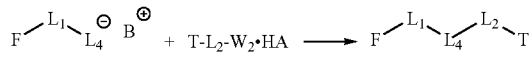

In certain embodiments, a HPP having Structure L-1 is prepared following Scheme 2 as described supra, wherein $L_4$ is C=O.

Preparation of N,N-diethylaminoethyl 9-cis-retinoate.HBr 30 g (0.1 mol) of sodium 9-cis-retinoate was dissolved in 100 ml of acetonitrile. 26.1 g (0.1 mol) of 2-Bromo-N,N-diethylethylamine.HBr was added into the reaction mixture. The mixture was stirred for overnight at RT. The solvents were evaporated off. 200 ml of ethanol was added into the residue. The solid was removed by filtration. The solution was evaporated to dryness. 100 ml of ethyl acetate was added into the reaction mixture. Hexane (100 ml) was added. The solid product was collected by filtration. After drying, it yielded 36 g of the desired product (75%). Hygroscopic product; solubility in water: 30 mg/ml; elementary analysis: $C_{26}H_{42}BrNO_2$; MW: 480.52; calculated % C, 64.99; H, 8.81; Br: 16.63; N, 2.91; O: 6.66. Found % C, 65.03; H, 8.80; Br: 16.60; N, 2.89; O: 6.68.

Preparation of N,N-diethylaminoethyl 13-cis-retinoate.HBr 30 g (0.1 mol) of sodium 13-cis-retinoate was dissolved in 100 ml of acetonitrile. 26.1 g (0.1 mol) of 2-Bromo-N,N-diethylethylamine.HBr was added into the reaction mixture. The mixture was stirred for overnight at RT. The solvents were evaporated off. 200 ml of ethanol was added into the residue. The solid was removed by filtration. The solution was evaporated to dryness. 100 ml of ethyl acetate was added into the reaction mixture. Hexane (100 ml) was added. The solid product was collected by filtration. After drying, it yielded 36 g of the desired product (75%). Hygroscopic product; solubility in water: 30 mg/ml; elementary analysis: $C_{26}H_{42}BrNO_2$; MW: 480.52; calculated % C, 64.99; H, 8.81; Br: 16.63; N, 2.91; O: 6.66. Found % C, 65.03; H, 8.80; Br: 16.59; N, 2.88; O: 6.70.

Preparation of N,N-Diethylaminoethyl all-trans-retinoate.Hbr 30 g (0.1 mol) of sodium all-trans-retinoate was dissolved in 100 ml of ace-tonitrile. 26.1 g (0.1 mol) of 2-Bromo-N,N-diethylethylamine.HBr was added into the reaction mixture. The mixture was stirred for overnight at RT. The solvents were evaporated off. 200 ml of ethanol was added into the residue. The solid was removed by filtration. The solution was evaporated to dryness. 100 ml of ethyl acetate was added into the reaction mixture. Hexane (100 ml) was added. The solid product was collected by filtration. After drying, it yielded 35 g of the desired product (72.9%). Hygroscopic product; elementary analysis: C H BrNO; MW: 480.52; calculated % C, 64.99; H, 8.81; Br: 16.63; N, 2.91; O: 6.66. Found % C, 65.03; H, 8.80; Br: 16.60; N, 2.89; O: 6.68.

Preparation of Retinyl N,N-dimethyl-2-aminoacetate.HCl 28.6 g (0.1 mol) of retinol was dissolved in 300 ml of acetonitril. 25 ml of triethylamine was added into the reaction mixture. 16 g of N,N-dimethylaminoacetyl chloride hydrochloride was added into the reaction mixture. The mixture was stirred for 5 h at RT. The solid was removed by filtration. The solution was evaporated to dryness. 500 ml of ethyl acetate was added into the residue. 200 ml of 5% of sodium carbonate solution was added into the mixture with stirring. The organic solution was collected and washed with water. After drying, it yielded 31 g of the desired product (75.5%). Hygroscopic product; elementary analysis: C H ClNO; MW: 408.02; calculated % C, 70.65; H, 9.39; Cl: 8.69; N, 3.43; O: 7.84. Found % Q70.60; H, 9.46; Cl: 8.71; N, 3.42; O: 7.81.

Preparation of N,N-diethylaminoethyl-4-[I-(5,6,7,8-tetrahydro-3,5,5,8,8-pentamethyl-2-naphthalenyl)ethenyl]benzoate.HCl 34.9 g (0.1 mol) of 4-[I-(5,6,7,8-tetrahydro-3,5,5,8,8-pentamethyl-2-naphthalenyl)ethenyl]benzoic acid (bexarotene, Targretin®) was dissolved in 300 ml of chloroform. 20.6 g of N,N'-Dicyclohexylcarbodiimide was added into the reaction mixture. 11.6 g of dimethylaminoethanol was added into the reaction mixture. The mixture was stirred for 3 hours at RT. The solid was removed by filtration. The chloroform solution was washed with 5% NaHCO (2×100 ml) and water (3×100 ml). The organic solution was dried over anhydrous sodium sulfate. Sodium sulfate was removed by filtration. 3.6 g of HCl gas in ether (100 ml) was added into the reaction mixture with stirring. The solid product was collected by filtration. After drying, it yielded 40 g of the desired product (85.8%). Hygroscopic product; elementary analysis: C H ClNO; MW: 484.11; calculated % C, 74.43; H, 8.74; Cl, 30 42 27.32; N, 2.89; O: 6.61. Found % C, 74.39; H, 8.76; Cl: 7.29; N, 2.91, O: 6.65.

Example 2

HPPs of Retinoids and Retinoid-Related Compounds have Higher In Vitro Penetration Rates Across Human Skin Comparing to their Parent Drugs Penetration rates of HPPs and their parent drugs through human skin were measured in vitro by modified Franz cells. A Franz cell had two chambers, the top sample chamber and the bottom receiving chamber. The human skin tissue (360-400 μm thick) that separated the top and the receiving chambers was isolated from the anterior or posterior thigh areas.

A compound tested (0.2 mL, 5% in 0.2 M phosphate buffer, pH 7.4) were added to the sample chamber of a Franz cell. The receiving chamber contains 2 ml of 2% bovine serum albumin in saline which was stirred at 600 rpm. The amount of the tested compound penetrating the skin was determined by high-performance liquid chromatography (HPLC) method. The results were shown in FIG. 1. The apparent flux values of the tested compounds were calculated from the slopes in the FIG. 1 and summarized in Tables 1.

Because the lowest detectable apparent flux values in this method was 1 μg/cm$^2$/h, parent drugs that showed a apparent flux value equal to or less than 1 μg/cm$^2$/h were considered as not detectable for penetrating across the skin tissue. The apparent flux values of these parent drugs (e.g. bexaroten (Targretin®)) were 1 μg/cm$^2$/h, therefore they were not detectable for penetrating across the skin tissue. However, their HPPs had detectable apparent flux value (0.35 mg/cm$^2$/h for HPP of bexaroten.) For the parents drugs that had a detectable apparent flux value, their HPPs have a higher detectable apparent flux values respectively. Therefore the HPPs of retinoids or retinoid-related compounds showed a higher penetration rate across the skin tissue comparing to their parent compounds.

TABLE 1

In vitro Penetration Rate of HPPs and their Parent Compounds

| HPPs | mg/cm$^2$/h | Parent compounds | mg/cm$^2$/h |
|---|---|---|---|
| 9-cis-retinoic acid 1-piperidineethyl ester•HBr | 0.67 | 9-cis-retinoic acid (alitretinoin) | 0.005 |
| N,N-diethylaminoethyl 13-cis-retinoate•HBr | 0.85 | 13-cis-retinoic acid (isotretinoin) | 0.005 |
| N,N-diethylaminoethyl all-trans-retinoate•HBr | 1.25 | all-trans-retinoic acid (tretinoin) | 0.005 |
| retinyl N,N-dimethyl-2-aminoacetate•HCl | 1.21 | vitamin A (retinol) | 0.005 |
| N,N-diethylaminoethyl 4-[1-(5,6,7,8-tetrahydro-3,5,5,8,8-pentamethyl-2-naphthalenyl)ethenyl]benzoate•HCl | 0.35 | bexaroten (Targretin ®) | 0.001 |

Example 3

Irritative Effect or Discomfort of the HPP or HPC on Skin of Mice

Irritative effect or discomfort in the skin of mice of HPPs of retinoids or retinoid-related compounds was evaluated during a period of 1 week after the topical application of 0.1 ml of 0.5% of the respective test drug in pH 7.4 phosphate buffer (0.2 M) to the back of nude mice twice per day. None of any signs of irritative effect or discomfort was observed for N,N-diethylaminoethyl 9-cis-retinoate.HBr (5% solution, A), N,N-diethylaminoethyl 13-cis-retinoate.HBr (5% solution, B), N,N-diethylaminoethyl all-trans-retinoate.HBr (5% solution, C), retinyl N,N-dimethyl-2-aminoacetate.HCl (5% solution, D), or N,N-diethylaminoethyl 4-[1-(5,6,7,8-tetrahydro-3,5,5,8,8-pentamethyl-2-naphthalenyl)ethenyl]benzoate.HCl.

Example 4

Conversion of HPPs to their Parent Drugs

HPPs of retinoids or retinoid-related compounds converted to the parent retinoids or retinoid-related compounds quickly in good yield in human plasma.

A HPP of retinoids or retinoid-related compound (10 mg) was dissolved in 0.1 ml of 0.2M pH 7.4 phosphate buffer. 1 ml of human plasma, preheated to 37° C., was added into the mixture. The mixture was kept in a water bath at 37° C., and at every 2 min intervals 0.2 ml of samples were withdrawn and added to 0.4 ml of methanol to precipitate the plasma protein. The samples were centrifuged for 5 min and analyzed by HPLC. The results showed that most of the HPPs of retinoids or retinoid-related compounds were converted back to the parent retinoids or retinoid-related compounds (Table 2).

TABLE 2

Half life of HPPs in plasma

| HPP | Parent drug | Half life (min) |
|---|---|---|
| N,N-diethylaminoethyl 9-cis-retinoate•HBr | | 12 +/− 1 |
| N,N-diethylaminoethyl 13-cis-retinoate•HBr | | 13 +/− 1 |

TABLE 2-continued

Half life of HPPs in plasma

| HPP | Parent drug | Half life (min) |
|---|---|---|
| N,N-diethylaminoethyl all-trans-retinoate•HBr | | 11 +/− 1 |
| retinyl N,N-dimethyl-2-aminoacetate•HCl | | 20 +/− 1 |
| N,N-diethylaminoethyl 4-[1-(5,6,7,8-tetrahydro-3,5,5,8,8-pentamethyl-2-naphthalenyl)ethenyl]benzoate•HCl | | 15 +/− 1 |

Example 5

Treatment of Clinical Mastitis Using HPPs of Retinoids or Related Compounds

Without being bounded by any theory, it is believed that Targretin (bexarotene) selectively activates a subclass of retinoid receptors called RXRs, which play an important role in several cellular activities. One of the most important of these activities is called programmed cell death, or "apoptosis," a natural process by which the body rids itself of unwanted cells. Targretin is being developed by Ligand in both topical and oral formulations. Topical Targretin is used for the treatment of cutaneous T-cell lymphoma (CTCL). In addition, Targretin oral formulation is used for the treatment of CTCL, head and neck carcinoma, systemic Kaposi's sarcoma, lung cancer, ovarian cancer, prostate cancer, and renal cell cancer.

Without being bounded by any theory, it is believed that alitretinoin (9-cis-retinoic acid) is a naturally-occurring endogenous retinoid that binds to and activates all known intracellular retinoid receptor subtypes (RARa, RARb, RARg, RXRa, RXRb and RXRg). Once activated these receptors function as transcription factors that regulate the expression of genes that control the process of cellular differentiation and proliferation in both normal and neoplastic cells. Alitretinoid is used for treatment of Kaposi's Sarcoma, AIDS-Related Kaposi's Sarcoma, other skin cancer, breast cancer, and other cancers.

For evaluation of antitumor activity, a human acute promyelocytic leukemia (APL) line derived from a patient with acute promyelocytic leukemia (APL) was implanted into mice. The experiment was carried out on 13 groups of mice: control group (A, administered orally with 0.1 ml of ethanol), groups administered with all-trans-retinoic acid (5 mg/kg or 10 mg/kg in 0.1 ml of ethanol, $B_1$ or $B_2$ respectively, orally), groups administered with all-trans-retinoic acid 1-piperidineethyl ester.HBr (5 mg/kg or 10 mg/kg in 0.1 ml of ethanol, $C_1$ or $C_2$ respectively, transdermally), groups administered with 9-cis-retinoic acid (5 mg/kg or 10 mg/kg in 0.1 ml of ethanol, $D_1$ or $D_2$ respectively, orally), groups administered with 9-cis-retinoic acid 2-pyrrolidinemethyl ester.HBr (5 mg/kg or 10 mg/kg in 0.1 ml of ethanol, $E_1$ and $E_2$ respectively, transdermally), groups administered with bexaroten (5 mg/kg or 10 mg/kg in 0.1 ml of ethanol, $F_1$ or $F_2$ respectively, orally), and groups administered with 4-[1-(5,6,7,8-pentamethyl-2-naphthalenyl)ethenyl]benzoic acid 1-pyrrolidinemethyl ester.HCl (5 mg/kg or 10 mg/kg in 0.1 ml of ethanol, $G_1$ and $G_2$ respectively, transdermally). The results showed that the prodrugs of retinoids demonstrated strong antitumor activity at as low as 5 mg/kg dose when they were administered transdermally (Table 3).

TABLE 3

Extension of survival period of acute promyelocytic leukemia mice by use of retinoids and their novel prodrugs.

| Compounds | Dose (mg/kg) perday | n | Survival Period (days) | Life Elongation Rate(%) | None Disease Rate at day 160 |
|---|---|---|---|---|---|
| Control (A) | — | 7 | 31.5 ± 2.9 | 100 | 0/7 |
| $B_1$ | 5 mg | 7 | 49.7 ± 3.6 | 158 | 0/7 |
| $B_2$ | 10 mg | 7 | 78.5 ± 3.7 | 249 | 2/7 |
| $C_1$ | 5 mg | 7 | 87.8 ± 3.4 | 278 | 4/7 |
| $C_2$ | 10 mg | 7 | 135.2 ± 5.9 | 429 | 5/7 |
| $D_1$ | 5 mg | 7 | 45.5 ± 2.3 | 144 | 1/7 |
| $D_2$ | 10 mg | 7 | 65.2 ± 4.1 | 207 | 3/7 |
| $E_1$ | 5 mg | 7 | 72.5 ± 4.6 | 230 | 3/7 |
| $E_2$ | 10 mg | 7 | 121.2 ± 4.8 | 385 | 5/7 |
| $F_1$ | 5 mg | 7 | 64.5 ± 3.7 | 205 | 3/7 |
| $F_2$ | 10 mg | 7 | 95.2 ± 3.9 | 302 | 5/7 |
| $G_1$ | 5 mg | 7 | 96.5 ± 4.4 | 306 | 5/7 |
| $G_2$ | 10 mg | 7 | 166.5 ± 5.4 | 529 | 6/7 |

Example 6

Antitumor Activity of HPP/HPC of Retinoid or Retinoid-Related Compound

For evaluation of antitumor activity of these prodrugs, human breast cancer cells (BCAP-37) were implanted into nude mice (BALB). After 3 days, 50 μl of 1% N,N-diethylaminoethyl 9-cis-retinoate.HBr and N,N-diethylaminoethyl 4-[1-(5,6,7,8-tetrahydro-3,5,5,8,8-pentamethyl-2-naphthalenyl)ethenyl]benzoate.HCl in 0.2M pH 7.4 phosphate buffer were topically applied to human breast cancer cells-implanted area (near the front leg) twice per day. After 20 days, the control group demonstrated 100% incidence (the average tumor size was 10 cm×10 cm), but none of tumor was seen in the test groups that treated with N,N-diethylaminoethyl 9-cis-retinoate.HBr or N,N-diethylaminoethyl 4-[1-(5,6,7,8-tetrahydro-3,5,5,8,8-pentamethyl-2-naphthalenyl)ethenyl]benzoate.HCl. Mice that were given the drugs did not show any discomfort or irritative effect. The average weight of the treated group was 25 grams and that of the control group was 21 grams. These prodrugs showed mild side effects.

In the third anti-tumor experiment, human colon cancer cells (LS174J, 2-3 mm³ of tumor tissue was used in each mouse) were subcutaneously xenografted into nude mice (BALB). After 10 days, the tumors grew to the size of 55 mm³ (0.055 ml). The experiment was carried out on 4 groups of mice: control group administered with ethanol (0.1 ml of ethanol, A, transdermally), group administered with all-trans-retinoic acid 1-piperidineethyl ester.HBr (10 mg/kg in 0.1 ml of ethanol, B, transdermally), group administered with 9-cis-retinoic acid 2-pyrrolidinemethyl ester.HBr (10 mg/kg in 0.1 ml of ethanol, C, transdermally), and group administered with 4-[1-(5,6,7,8-tetrahydro-3,5,5,8,8-pentamethyl-2-naphthalenyl)ethenyl]benzoic acid 1-pyrrolidinemethyl ester.HCl (10 mg/kg in 0.1 ml of ethanol, D, transdermally). The results showed that the pro-drugs of retinoids have very strong anti-tumor activity (Table 4).

TABLE 4

Anti-colon cancer activity of retinoids and their novel prodrugs.

| Compounds | Tumor size at day 10 (mm³) | Dose (mg/kg) perday | n | Survival Period (days) | Life Elongation Rate(%) | Tumor size at day 40 (mm³) |
|---|---|---|---|---|---|---|
| A | 52 ± 15 | 0 mg | 7 | 50.5 ± 5.2 | 100 | 1255 ± 65 |
| B | 55 ± 13 | 10 mg | 7 | 85.7 ± 7.6 | 170 | 675 ± 55 |
| C | 57 ± 19 | 10 mg | 7 | 81.5 ± 5.7 | 161 | 627 ± 49 |
| D | 56 ± 1 | 10 mg | 7 | 105.7 ± 5.8 | 209 | 487 ± 61 |

Example 7

Treatment of Psoriasis Using HPPs of Retinoids or Retinoid-Related Compounds

Heavy suspensions of Malassezia [Rosenberg, E. W., et al., Mycopathologia, 72, 147-154 (1980)] were applied to shaved skin on the backs of Chinese white rabbits (n=4×10) twice (at 7 am and 7 pm respectively) per day for 2 weeks. Lesions similar to psoriasis resulted. Then the same dosage of Malassezia was applied to the same area with a 0.5% aqueous solution of 200 μl of 0.05% N,N-diethylaminoethyl 9-cis-retinoate.HBr or all-trans-retinoic acid 1-piperidineethyl ester.HBr being applied to the same areas 3 hours (10 am and 10 pm) after the application of Malassezia (7 am and 7 pm). The control group was only applied with Malassezia. 10 days after the application of both the Malassezia and the HPPs, the lesions of the groups that were treated with HPPs were resolved, and the lesions in the control groups became worse.

Example 8

Treatment of Acute Promyelocytic Leukemia 5 ml of 1% N,N-diethylaminoethyl 9-cis-retinoate.HCl in 50% ethanol is sprayed to skin on chest, back, or any part of the body twice per day and 10 ml/m² of (8S,10S)-8-acetyl-10-[(2S,4S,5S,6S)-4-amino-5-acetoxy-6-methyl-oxan-2-yl]oxy-6,8,11-triacetoxy-1-methoxy-9,10-dihydro-7H-tetracene-5,12-dione.HCl (tetraacetyl daunorubicin.HCl) is administered in a rapid intravenous infusion for 30 days or until the disease is cured.

Example 9

Treatment of Breast Cancer 0.5 ml of 2% N,N-diethylaminoethyl 4-[1-(5,6,7,8-tetrahydro-3,5,5,8,8-pentamethyl-2-naphthalenyl)ethenyl]benzoate.HCl in 50% ethanol is sprayed to skin on the tumor, 1 hour later, 0.5 ml of 0.5% (8S,10S)-8-acetyl-10-[(2S,4S,5S,6S)-4-amino-5-acetoxy-6-methyl-oxan-2-yl]oxy-6,8,11-triacetoxy-1-methoxy-9,10-dihydro-7H-tetracene-5,12-dione.HCl (tetraacetyl daunorubicin.HCl ) in 50% ethanol is sprayed on the same area of skin on the tumor. The process is repeated three times per day and the treatment is continued until the tumor disappeared.

Example 10

Treatment of Prostate Cancer 0.5 ml of 2% N,N-diethylaminoethyl all-trans-retinoate.HCl in 50% ethanol is sprayed to skin on the pubic area, 1 hour later, 0.5 ml of 0.5% (8S,10S)-10-(4-amino-5-acetoxy-6-methyl-tetrahydro-2H-pyran-2-yloxy)-6,8,11-triacetoxy-8-(2-acetoxyacetyl)-1-methoxy-7,8,9,10-tetrahydrotetracene-5,12-dione.HCl (pentaacetyl doxorubicin.HCl) in 50% ethanol is sprayed on the same area of skin on the pubic area. The process is repeated three times per day and the treatment is continued until the cancer is cured.

Example 11

Treatment of Lung Cancer 0.5 ml of 2% N,N-diethylaminoethyl all-trans-retinoate.HCl in 50% ethanol are sprayed to skin on chest, 1 hour later, 0.5 ml of 0.5% (8S,10S)-10-(4-amino-5-acetoxy-6-methyl-tetrahydro-2H-pyran-2-yloxy)-6,8,11-triacetoxy-8-(2-acetoxyacetyl)-1-methoxy-7,8,9,10-tetrahydrotetracene-5,12-dione.HCl (pentaacetyl doxorubicin.HCl ) in 50% ethanol is sprayed on the same area of skin on the chest. The process is repeated three times per day and the treatment is continued until the disease is cured.

Example 12

Treatment of Lung Cancer 0.5 ml of 2% N,N-diethylaminoethyl all-trans-retinoate.HCl in 50% ethanol is inhaled into the lung, 1 hour later, 0.5 ml of 0.5% (8S,10S)-10-(4-amino-5-acetoxy-6-methyl-tetrahydro-2H-pyran-2-yloxy)-6,8,11-triacetoxy-8-(2-acetoxyacetyl)-1-methoxy-7,8,9,10-tetrahydrotetracene-5,12-dione.HCl (pentaacetyl doxorubicin.HCl ) in 50% ethanol is inhaled to lung. The process is repeated three times per day and the treatment is continued until the disease is cured.

Example 13

Treatment of Skin Cancer 1 ml of 2% N,N-diethylaminoethyl all-trans-retinoate.HCl in 50% ethanol is sprayed to the skin having skin cancer three times per day and the treatment is continued until the disease is cured.

Example 14

Treatment of Acne Vulgaris 1 ml of 0.5% N,N-diethylaminoethyl all-trans-retinoate.HCl in 50% ethanol is applied to skin with acne vulgaris three times per day and the treatment is continued until the condition is cured.

Example 15

Treatment of Psoriasis 3 ml of 0.5% N,N-diethylaminoethyl 9-cis-retinoate.HCl in 50% ethanol is applied to skin with psoriasis three times per day and the treatment is continued until the disease is cured.

Example 16

Treatment of the Smoking Disease Emphysema 3 ml of 1% N,N-diethylaminoethyl all-trans-retinoate.HCl in 50% ethanol is applied to the skin on the chest three times per day and the treatment is continued until the disease is cured.

Example 17

Treatment of the Smoking Disease Emphysema 3 ml of 1% N,N-diethylaminoethyl all-trans-retinoate.HCl in 50% ethanol is inhaled to the lung three times per day and the treatment is continued until the disease is cured.

Example 18

Treatment for Severe Lung Disease, Chronic Obstructive Pulmonary Disease (COPD)

3 ml of 1% N,N-diethylaminoethyl all-trans-retinoate.HCl in 50% ethanol is applied to skin on the chest three times per day and the treatment is continued until the disease is cured.

Example 19

Treatment for Severe Lung Disease, Chronic Obstructive Pulmonary Disease (COPD)

3 ml of 1% N,N-diethylaminoethyl all-trans-retinoate.HCl in 50% ethanol is inhaled to the lung three times per day and the treatment is continued until the disease is cured.

What is claimed is:

1. A high penetration composition having a compound of the following chemical structure:

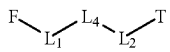

Structure L-1 including stereoisomers and pharmaceutically acceptable salts thereof, wherein:

F has a structure of Structure F1

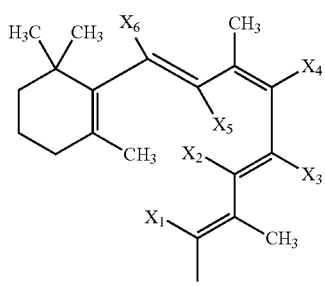

Structure F1 including stereoisomers and pharmaceutically acceptable salts thereof, wherein:

$X_1$-$X_6$ are independently selected from the group consisting of H, OH, Cl, Br, F, I, substituted and unsubstituted alkyl, substituted and unsubstituted perfluoroalkyl, and substituted and unsubstituted alkyloxy;

HA is selected from the group consisting of hydrochloride, hydrobromide, hydroiodide, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid and pamoic acid;

T is Structure Na:

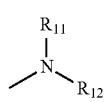

Structure Na each $R_{11}$-$R_{12}$ is independently selected from the group consisting of H, $CH_2COOR_{11}$, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide wherein any carbon may be further independently replaced with O, S, P, or $NR_{11}$;

$L_1$ is nothing;

$L_2$ is —O—$L_3$;

$L_4$ is C=O;

$L_3$ is selected from the group consisting of $CH_2COOL_6$, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide any carbon may be further independently replaced with O, S, P, or $NL_3$;

$L_5$ is selected from the group consisting of nothing, $CH_2COOL_6$, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon may be further independently replaced with O, S, P, or $NL_3$;

$L_6$ is selected from the group consisting of substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon may be further independently replaced with O, S, N, P(O)OL$_7$, CH=CH, C≡C, CHL$_7$, CL$_5$L$_7$, aryl, heteroaryl, or cyclic groups; and L$_7$ is selected from the group consisting of substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon may be further independently replaced with O, S, N, P(O)OL$_6$, CH=CH, C≡C, CHL$_6$, CL$_6$L$_5$, aryl, heteroaryl, or cyclic groups.

2. The high penetration composition of claim 1 comprising a structure of Structure 1:

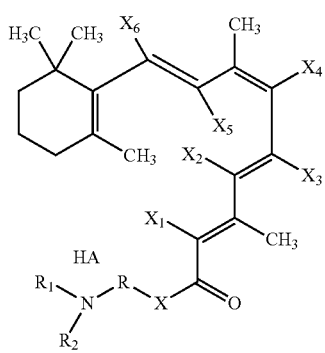

Structure 1 including stereoisomers and pharmaceutically acceptable salts thereof, wherein:

R$_1$ is selected from the group consisting of H, substituted and unsubstituted alkyl, substituted and unsubstituted alkyloxyl, substituted and unsubstituted alkenyl, substituted and unsubstituted alkynyl, substituted and unsubstituted aryl and substituted and unsubstituted heteroaryl residues;

R$_2$ is selected from the group consisting of H, substituted and unsubstituted alkyl, substituted and unsubstituted alkyloxyl, substituted and unsubstituted alkenyl, substituted and unsubstituted alkynyl, substituted and unsubstituted aryl and substituted and unsubstituted heteroaryl residues;

X is O; and

R is selected from the group consisting of substituted and unsubstituted alkyl, substituted and unsubstituted alkoxyl, substituted and unsubstituted perfluoroalkyl, substituted and unsubstituted alkyl halide, substituted and unsubstituted alkenyl, substituted and unsubstituted alkynyl, substituted and unsubstituted aryl, and substituted and unsubstituted heteroaryl.

3. A pharmaceutical composition comprising a high penetration composition according to claim 1 and a pharmaceutically acceptable carrier.

4. The pharmaceutical composition according to claim 3, wherein the pharmaceutically acceptable carrier is polar.

5. The pharmaceutical composition according to claim 3, wherein the pharmaceutically acceptable carrier is selected from the group of alcohol, acetone, ester, water, and aqueous solution.

6. A method for penetrating a biological barrier, comprising administering to the biological barrier a pharmaceutical composition according to claim 3.

7. A method for treating a condition in a subject, comprising administering to the subject the high penetration composition according to claim 1; wherein the condition is a tumor selected from the group consisting of benign tumor, breast cancer, colon-rectum cancer, lung cancers, skin cancer, basal cell carcinoma, cervical cancer, mycosis fungoides, Kaposi's sarcoma, AIDS-related Kaposi's sarcoma, systemic Kaposi's sarcoma, cutaneous T-cell lymphoma (CTCL), squamous cell skin cancer, head and neck carcinoma, ovarian cancer, prostate cancer, and renal cell cancer.

* * * * *